US010639387B2

(12) United States Patent
Bonutti et al.

(10) Patent No.: US 10,639,387 B2
(45) Date of Patent: May 5, 2020

(54) SYSTEMS AND METHODS FOR DISINFECTION

(71) Applicant: P Tech, LLC, Effingham, IL (US)

(72) Inventors: Peter M. Bonutti, Manalapan, CA (US); Justin Beyers, Effingham, IL (US); Tonya M. Bierman, Dieterich, IL (US)

(73) Assignee: P Tech, LLC, Effingham, IL (US)

( * ) Notice: Subject to any disclaimer, the term of this patent is extended or adjusted under 35 U.S.C. 154(b) by 0 days.

(21) Appl. No.: 16/025,152

(22) Filed: Jul. 2, 2018

(65) Prior Publication Data

US 2019/0134242 A1 May 9, 2019

Related U.S. Application Data

(63) Continuation of application No. 14/609,025, filed on Jan. 29, 2015, now Pat. No. 10,010,634.

(60) Provisional application No. 61/932,872, filed on Jan. 29, 2014.

(51) Int. Cl.
*A61L 2/10* (2006.01)
*C02F 1/32* (2006.01)
*C02F 1/36* (2006.01)
*A61L 2/025* (2006.01)

(52) U.S. Cl.
CPC .............. *A61L 2/10* (2013.01); *A61L 2/025* (2013.01); *C02F 1/325* (2013.01); *C02F 1/36* (2013.01); *C02F 2201/3222* (2013.01); *C02F 2201/3226* (2013.01); *C02F 2303/04* (2013.01)

(58) Field of Classification Search
CPC .. A61L 2/10; A61L 2/025; C02F 1/325; C02F 1/36; C02F 2201/3222; C02F 2201/3226; C02F 2303/04

USPC ... 250/428, 430, 431, 432 R, 433, 434, 435, 250/436, 438
See application file for complete search history.

(56) References Cited

U.S. PATENT DOCUMENTS

| | | | |
|---|---|---|---|
| 6,132,784 A | 10/2000 | Brandt et al. | |
| 8,426,800 B2 | 4/2013 | Ingram et al. | |
| 8,933,416 B2 | 1/2015 | Arcand et al. | |
| 2002/0153021 A1* | 10/2002 | Audet | A47L 15/0015 134/1 |
| 2003/0086817 A1* | 5/2003 | Horton, III | A61L 2/0011 422/24 |
| 2005/0028848 A1 | 2/2005 | Lai | |

(Continued)

FOREIGN PATENT DOCUMENTS

WO 02102421 A1 12/2002
WO 2009104119 A2 8/2009
(Continued)

OTHER PUBLICATIONS

International Search Report and Written Opinion, Application No. PCT/US15/13553, dated Apr. 13, 2015, pp. 9.

*Primary Examiner* — Nicole M Ippolito
*Assistant Examiner* — Hanway Chang
(74) *Attorney, Agent, or Firm* — Stinson LLP

(57) ABSTRACT

A disinfecting system includes a housing. An ultraviolet light (UV) source is secured to the housing and configured to emit UV light for disinfection of a target. A processor is secured to the housing in communication with the UV light source. The processor is configured to activate the UV light source for a selected amount of time suitable for disinfection of the target.

16 Claims, 20 Drawing Sheets

(56) References Cited

U.S. PATENT DOCUMENTS

| | | |
|---|---|---|
| 2006/0195165 A1* | 8/2006 | Gertner .............. A61N 5/0603 607/86 |
| 2008/0131337 A1 | 6/2008 | Lucas et al. |
| 2009/0274576 A1 | 11/2009 | Ressler |
| 2011/0024649 A1 | 2/2011 | Merkle |
| 2011/0117202 A1* | 5/2011 | Bourke, Jr. ........ H05B 41/2806 424/490 |
| 2011/0309032 A1 | 12/2011 | Maeki |
| 2012/0025096 A1* | 2/2012 | Lovenvirth .......... A01K 1/0107 250/455.11 |
| 2012/0153783 A1 | 6/2012 | Shoenfeld |
| 2012/0204800 A1 | 8/2012 | Beaudoin et al. |
| 2012/0223216 A1* | 9/2012 | Flaherty .................. A61L 2/10 250/214.1 |
| 2013/0045133 A1 | 2/2013 | Maguire |
| 2013/0270459 A1 | 10/2013 | Fontani |
| 2014/0328720 A1 | 11/2014 | Mano et al. |
| 2015/0090903 A1 | 4/2015 | Cole |
| 2015/0090904 A1 | 4/2015 | Cole |
| 2015/0231287 A1 | 8/2015 | Lin et al. |
| 2015/0297766 A9 | 10/2015 | Cole |
| 2015/0367008 A1 | 12/2015 | Romo et al. |
| 2016/0114067 A1 | 4/2016 | Dobrinsky et al. |

FOREIGN PATENT DOCUMENTS

| | | |
|---|---|---|
| WO | 2011143265 A2 | 11/2011 |
| WO | 2012032543 A1 | 3/2012 |
| WO | 2012084319 A1 | 6/2012 |

* cited by examiner

SYSTEMS AND METHODS FOR DISINFECTION

BACKGROUND

The field of the disclosure generally relates to principles of disinfection—which may include one or more of sanitization, sterilization, and cleaning—debridement, treatment of tissue wound surfaces with agents, optical and acoustic treatments with or without pharmaceutical/chemotherapeutic agents. The individual treatment or combination treatment may enhance existing single module treatment for management of cleansing disinfection, wound tissue care, etc.

Generally, improperly disinfected (e.g., sterilized) objects can be harmful to patients and/or users as the objects can potentially transfer or spread harmful agents (e.g. bacteria). In some instances, deaths have been caused by improperly sterilized objects. For example, an amoeba was introduced to patients' brains by the use of nasal rinsing apparatus having contaminated water. Additionally, improperly sterilized medical instruments have been known to transmit drug-resistant bugs and/or bacteria in hospitals possibly due to a complete removal of a bioburden. There is a need for systems and methods of sterilizing objects used on or by patients.

BRIEF DESCRIPTION

In one aspect, a disinfecting system includes a housing. An ultraviolet light (UV) source is secured to the housing and configured to emit UV light for disinfection of a target. A processor is secured to the housing in communication with the UV light source. The processor is configured to activate the UV light source for a selected amount of time suitable for disinfection of the target.

The features, functions, and advantages that have been discussed can be achieved independently in various embodiments or may be combined in yet other embodiments, further details of which can be seen with reference to the following description and drawings.

DETAILED DESCRIPTION

Figure 1:
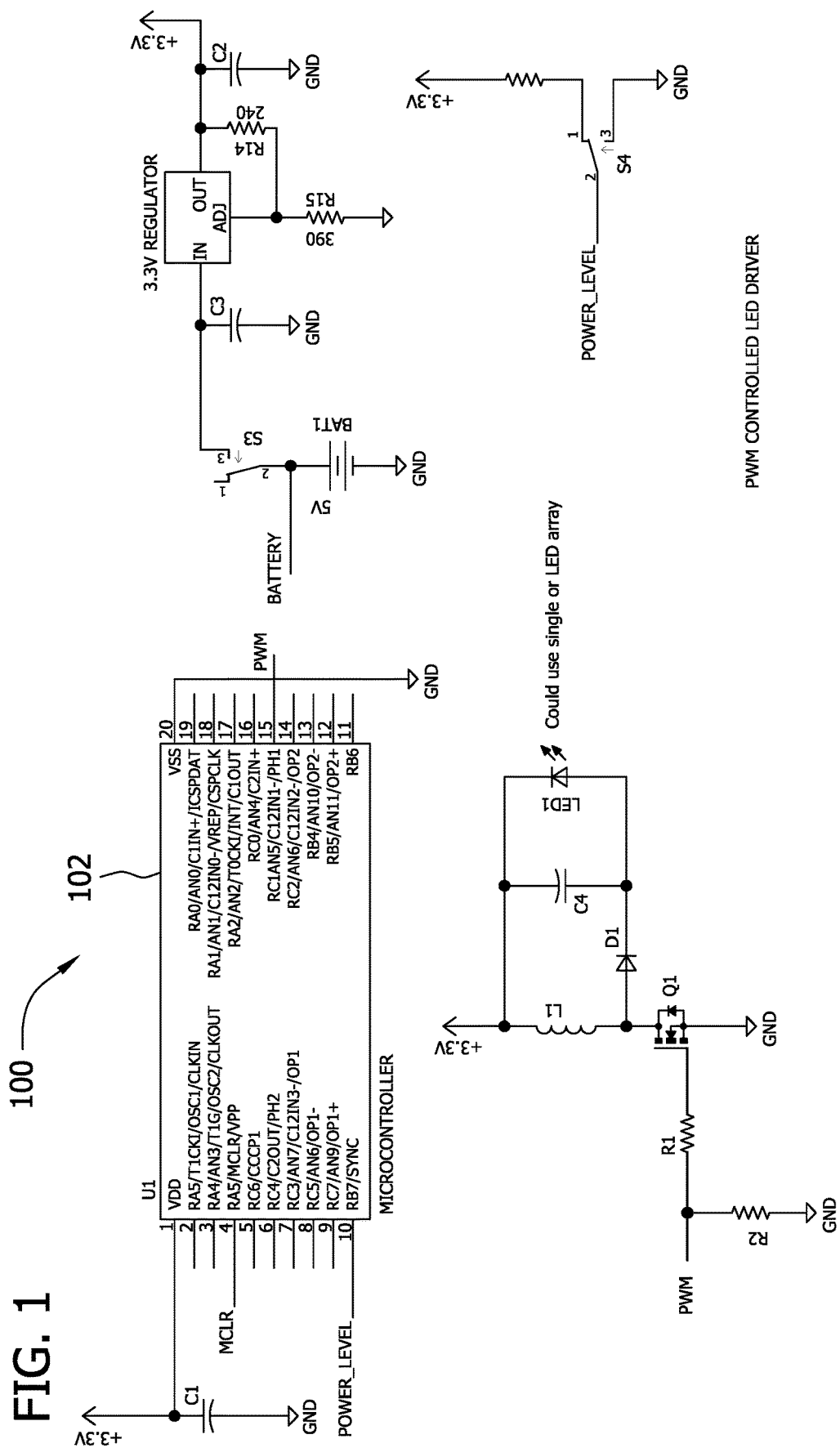
FIG. 1 is a schematic diagram of a pulse-width modulation (PWM) LED driver circuit.

The systems and methods described herein enable disinfecting of a target (e.g., one or more of an object, a surface, material, and matter) using ultraviolet (UV) light and/or ultrasound. As used herein, disinfecting and disinfection of the target means the ability to kill and/or destroy some or all infectious agent(s) at/on the target. Thus, disinfecting may include sterilization or sanitization, though not necessarily. The ultraviolet is configured to be effective in retarding growth, destroying, and/or killing infectious agents. As used herein, "infectious agent" or "infectious agents" refers to any organism that causes disease in a host including, but not limited to, a virus, bacterium, bacteria, prion, fungus, parasite, and disease (e.g. toxoplasmosis).

Ultraviolet light, such as ultraviolet C (UVC; i.e., electromagnetic radiation or light having a wavelength from about 100 nm to about 280 nm, such as 254 nm), has been known to have a microbicide and bactericidal effects on air, liquids, and surfaces. In some embodiments, a wavelength set to 254 nm is effective at eliminating bacteria (e.g. *Naegleria fowleri*) in the following lifecycle stages: Cyst, trophozoite, and flagellate. In such embodiments, the ultraviolet (UV) dosage utilized for the inactivation of the *N. fowleri* in water is 63 mW·sec/cm$^2$. Other electromagnetic radiation wavelengths may also be effective for disinfecting, sanitizing and/or sterilizing, including but not limited to wavelengths from about 270 nm to about 320 nm.

In one embodiment, ultraviolet light is transmitted in and around the embodiments described herein through an ultraviolet LED or LED array. In some embodiments, the LED is flexible and capable of flush securement on non-planar surfaces. Additionally, the LED array may be fabricated on a flexible strip. In some embodiments, a non-pulsed output is provided with the intensity controlled by a current limiting resistor in series with the LED. Alternatively, the UV light can be transmitted in any manner that facilitates sterilization as described herein, including but not limited to, a fluorescent UVC bulb and a laser. The ultraviolet LED(s) described herein can have a wavelength range of 100-400 nm. In some embodiments, a wavelength at 240-260 nm is preferred (i.e. for DNA absorption and/or bacteria/virus reduction), or at 365 nm (i.e. for water sterilization or treatment). Alternatively, the UVC described herein and used in various embodiments can scan in any suitable wavelength range that facilitates disinfection, sanitation, and/or sterilization as described herein. In the exemplary embodiment, a single or multiple sensors could be used to monitor temperature, power, pH, and/or other parameters needed to determine if the object that is subject to disinfection, sanitation, and/or sterilization is safe to use. The treatment time may be automated, and the movement of the UV light source and/or the object to be treated may be automated. For example, a robot or other device may automated movement of the UV light source and/or object to be treated.

FIG. 1 is a schematic diagram of a pulse-width modulation (PWM) LED driver circuit, generally indicated at reference numeral 100. Circuit 100 includes a processor 102 to control the output of the buck boost converter that drives the UV LED(s) 104 (e.g., UVC LED(s)). A switch is connected to the processor 102, which enables a user to set an intensity level of the UV LED(s). In some embodiments, circuit 100 is capable of driving high power UV LED(s). In the exemplary embodiment, the PWM UV LED is powered using a battery. Alternatively, the PWM UV LED can be powered by any known power source including, but not limited to, a DC power supply.

Figure 2:
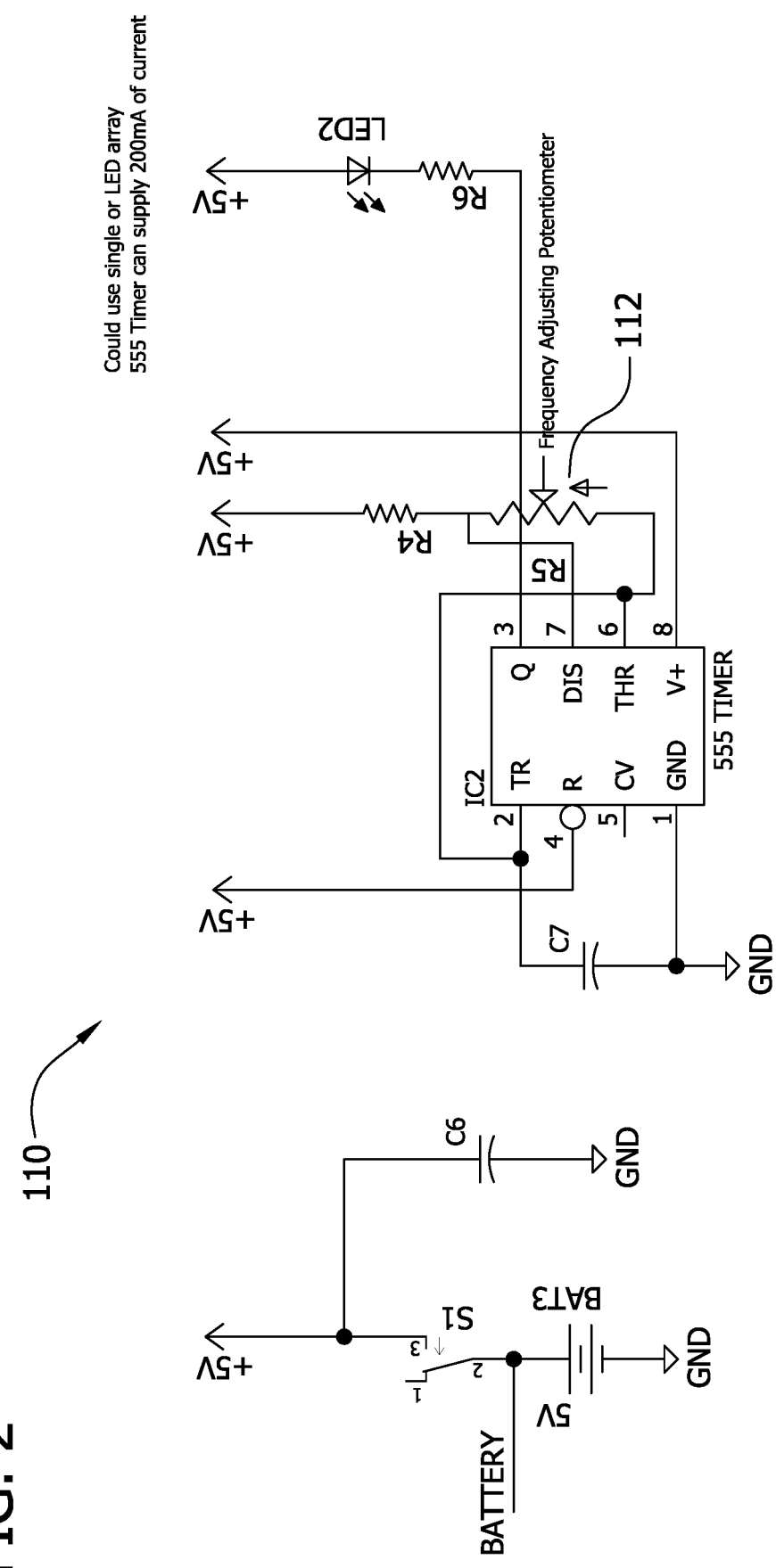
FIG. 2 is a schematic diagram of a 555 LED driver circuit for use with the circuit shown in FIG. 1.

FIG. 2 is a schematic diagram of a 555 LED driver circuit, generally indicated at reference numeral 110, for use with the circuit 100 shown in FIG. 1. The circuit 110 includes a 555 timer to drive the UV LED(s) 104. The intensity level of the UV LED(s) can be controlled by tuning the frequency adjusting potentiometer 112. The driver 110 will be capable of driving lower power UV LED(s). In the exemplary embodiment, circuit 110 is powered using a battery. Alternatively, circuit 110 can be powered by any known power source including, but not limited to, a DC power supply.

Figure 3:
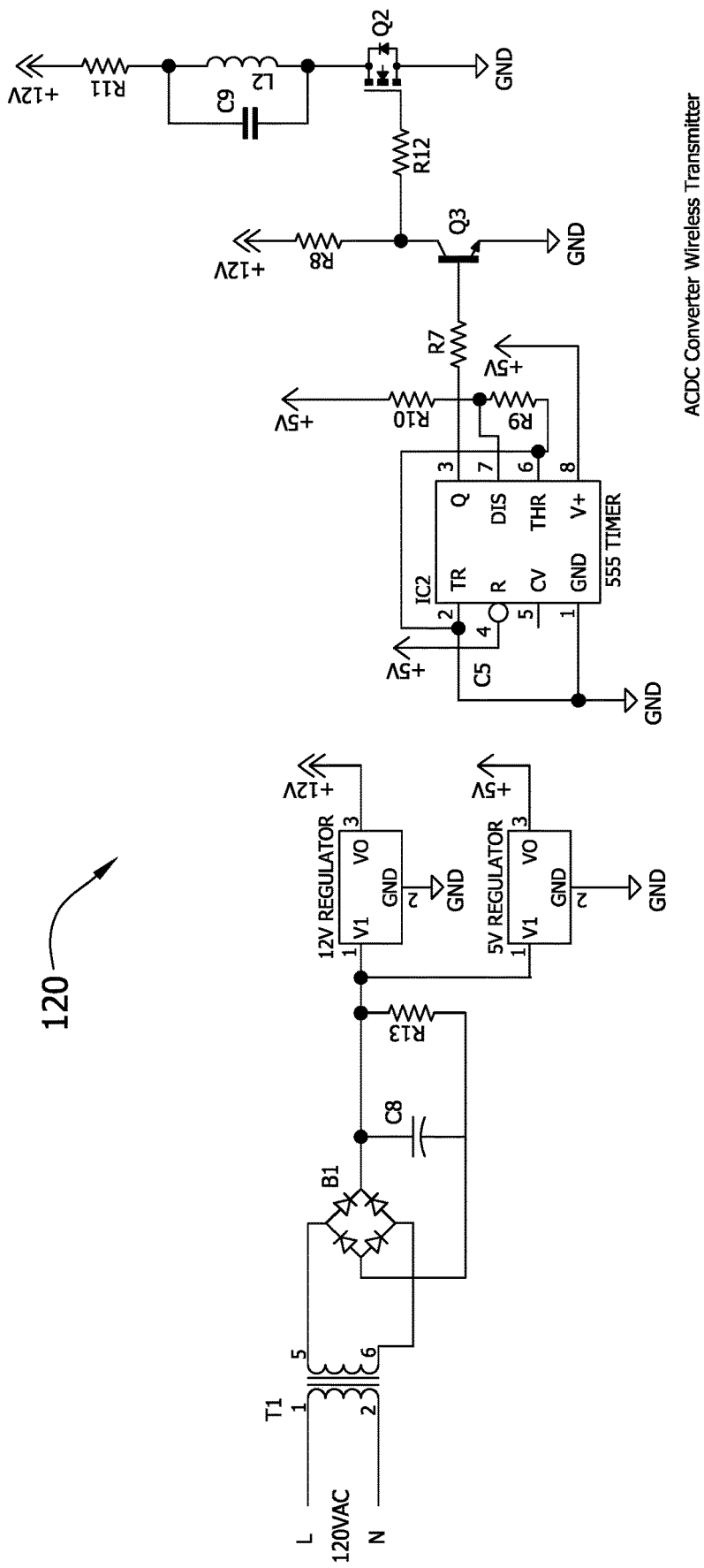
FIG. 3 is a schematic diagram of a wireless charging circuit for use with the circuits shown in FIGS. 1 and 2.

In one embodiment, the battery used to power circuits 100 and 110 could be charged using AC\DC wall adapter or wireless charging technology. FIG. 3 is a schematic diagram of a wireless charging circuit 120 for use with circuits 100 and 110 shown in FIGS. 1 and 2. In the exemplary embodiment, circuit 120 utilizes a transformer, rectifier circuit, and LDO regulators to power a 555 timer oscillator circuit, such as circuit 110. The oscillator circuit drives an inductor that will be used to transmit an electromagnetic field to a receiving circuit. The inductor L2 and capacitor C9 values will be chosen to resonate at the same frequency of the 555 timer.

Figure 4:
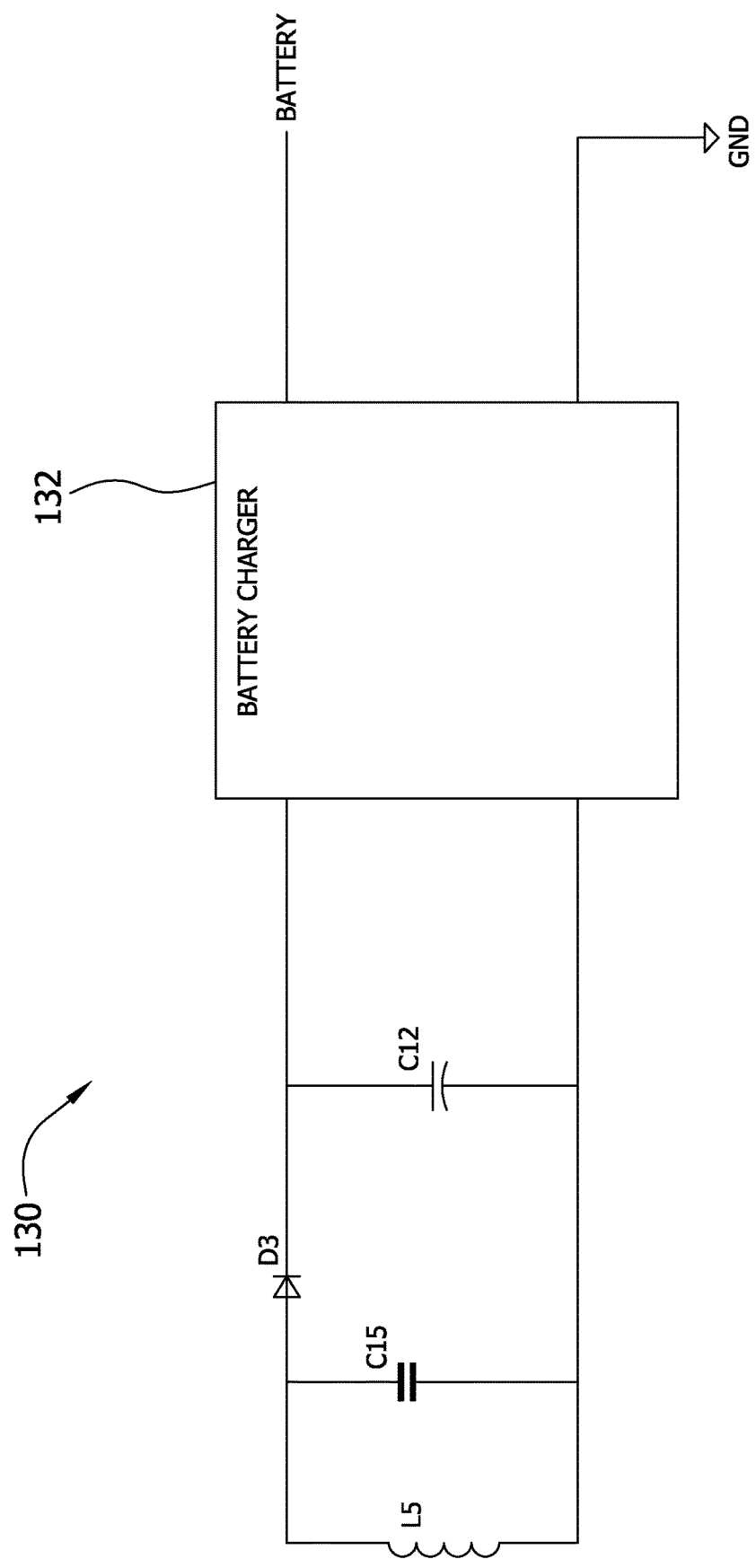
FIG. 4 is a schematic diagram of a wireless receiver circuit for use with the circuits shown in FIGS. 1-3.

FIG. 4 is a schematic diagram of a wireless receiver circuit 130 for use with circuits 100, 110, and 120 shown in FIGS. 1-3. In the exemplary embodiment, circuit 130 includes a battery charger 132 that powered by the wireless receiver. The wireless receiving circuit also includes an inductor L5 and capacitor C15 which values will be chosen to resonate at the same frequency as the transmitter circuit. The half-wave rectifier and filter capacitor will be used to power the battery charger 132. Alternatively, the battery charger 132 can be powered using an AC/DC power source. In one embodiment, the battery charger 132 is used to charge the battery that powers the LED driver circuit 100.

Figure 5:
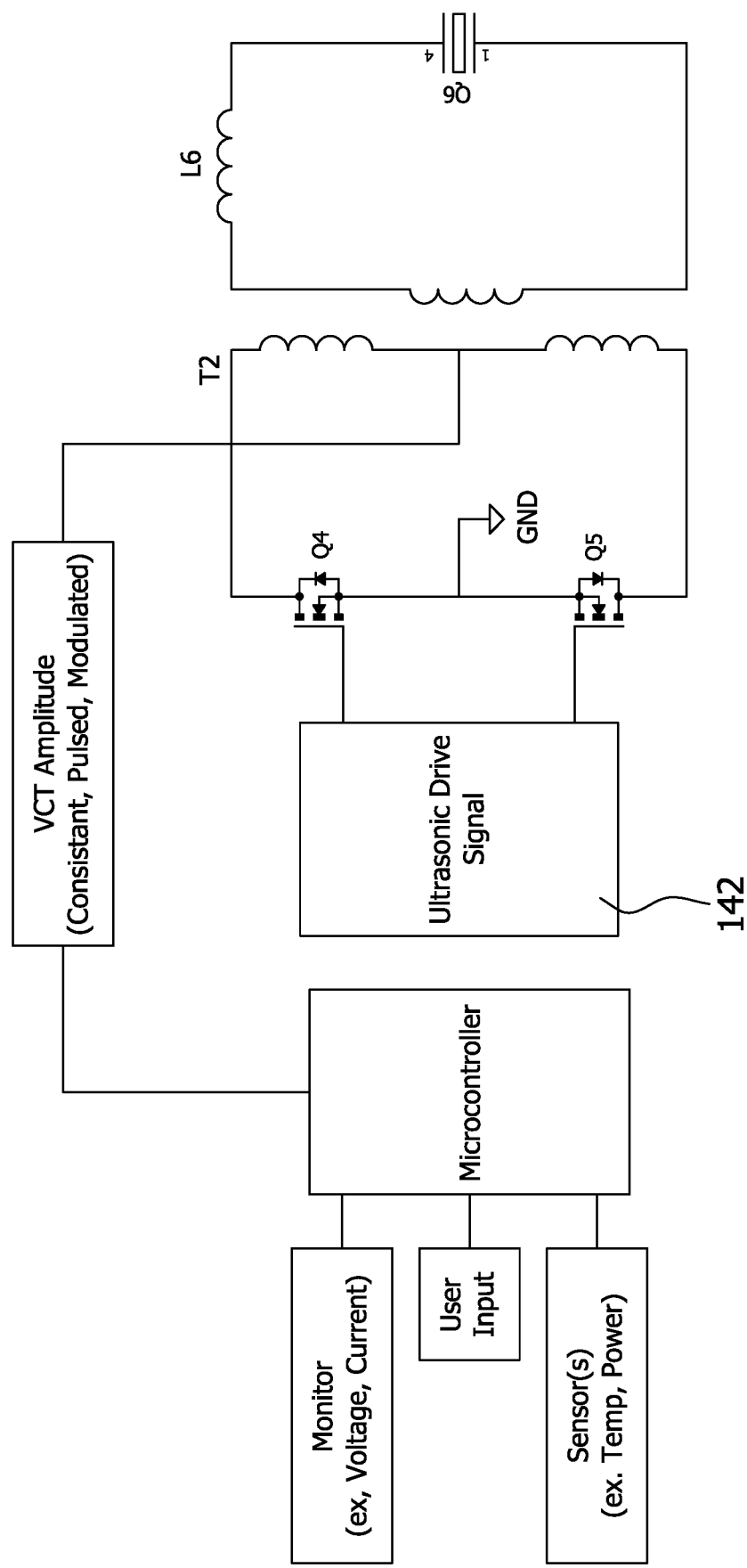
FIG. 5 is a schematic diagram of an ultrasonic drive circuit that can be used with any combination of the circuits shown in FIGS. 1-4.

In addition to the sterilization provided by UV, ultrasound can be combined with the UV to clean and/or sterilize objects. FIG. 5 is a schematic diagram of an ultrasonic drive circuit 140 that can be used with any combination of circuits 100, 110, 120, and 130 shown in FIGS. 1-4. In one aspect, ultrasonic acoustic waves pass through liquids, such as water, causing cavitation. Cavitation is the formation of small high pressure bubbles. When the bubbles implode or explode the high level of pressure and heat is exerted onto nearby surfaces. Cavitation can be used to disrupt and destroy infectious agents on, in, and/or around an object. Additionally, ultrasound can be used to disrupt intercellular communication which can prevent growth of and break apart infectious agents without the use of cavitation.

In some embodiments, a frequency range of the ultrasound is adjusted to target specific infectious agents. In one embodiment, the ultrasound is adjusted in the frequency range from 20 kHz to 3 MHz. Alternatively, the frequency range can be any range that facilitates sterilization as described herein. In the exemplary embodiment, the drive signal is selected to have a predetermined output based on the target object. For example, the predetermined output of the drive signal can be constant, pulsed, and/or modulated to obtain the desired results. The ultrasonic device can be made of many different constructions including, but not limited to, bolt clamped Langevin or piezoelectric discs. In some embodiments, one or more sensors are used to monitor at least one of temperature, power, pH, and other parameters needed to determine if the ultrasound is or has been effective in sterilizing an object.

In the exemplary embodiment, circuit 140 includes a processor 142 to control the drive signal of an ultrasonic transducer. The push-pull design consist of two mosfets being switch to cause a push and pull of current through the primary side of the transformer. The center tap on the primary side of the transformer determines amplitude on the secondary side of the transformer. The inductor on the secondary side of the transformer will be used for impedance matching to allow for efficient power consumption. Other drive circuits as known in the art can be utilized.

It should be noted that processors described herein may include one or more processing units (e.g., in a multi-core configuration). Further, processors described herein may be implemented using one or more heterogeneous processor systems in which a main processor is present with secondary processors on a single chip. As another illustrative example, the processors may be a symmetric multi-processor system containing multiple processors of the same type. Further, the processors may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein. Additionally, the processors may perform partial processing and receive partial processing by a processor and/or computing device communicatively coupled to the processors.

Figure 6:
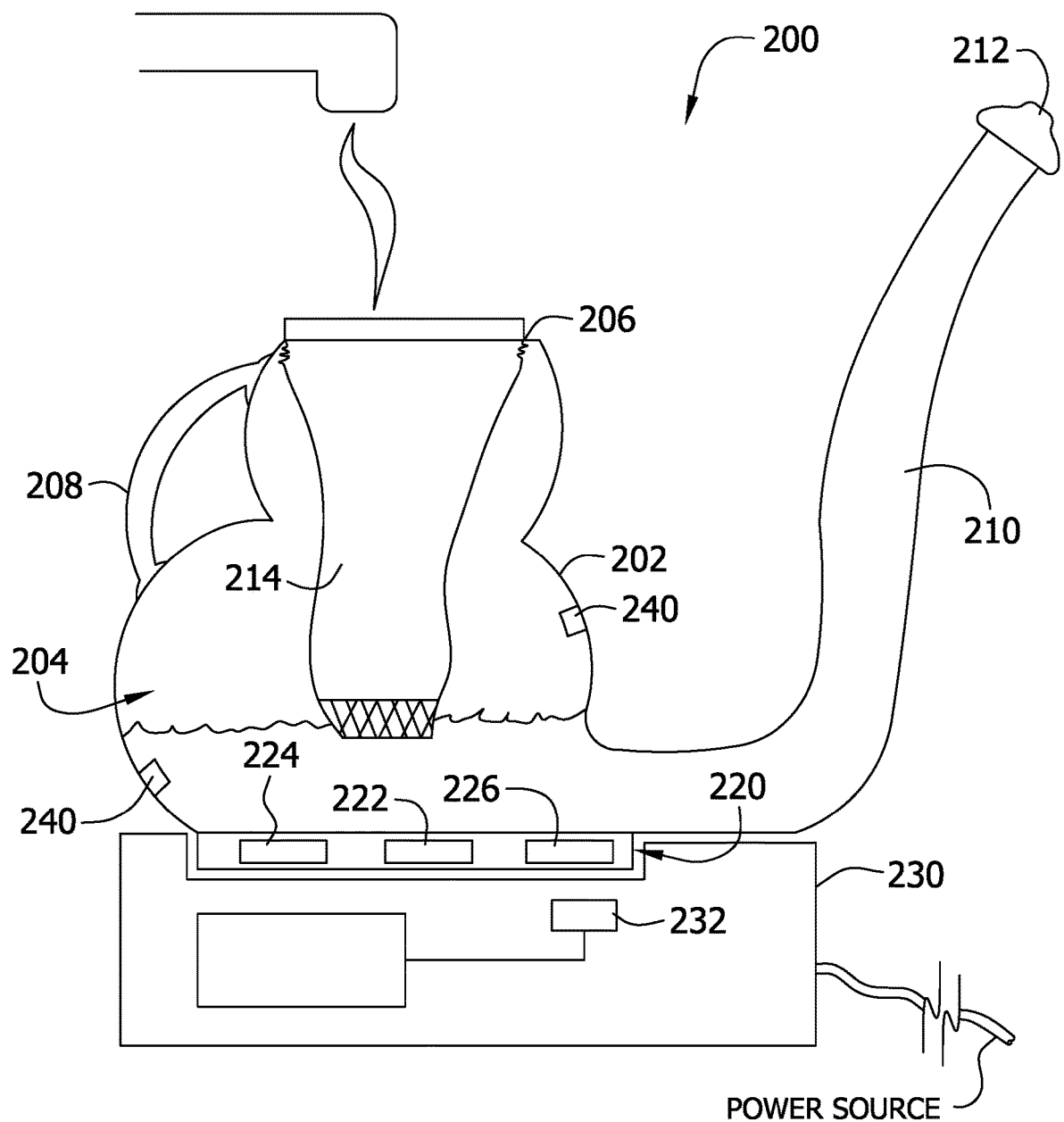
FIG. 6 is a perspective view of an exemplary nasal cavity fluid dispenser for use with any combination of the circuits shown in FIGS. 1-5.

FIG. 6 is a perspective view of an exemplary nasal cavity fluid dispenser 200 for use with any combination of circuits 100, 110, 120, 130, and 140 shown in FIGS. 1-5. In one embodiment, dispenser 200 is configured to disperse fluid into a nasal cavity for nasal irrigation (e.g. Neti pot). In the exemplary embodiment, dispenser 200 includes a main body 202, fluid reservoir 204, and a fluid entry aperture 206. Connected to the main body 202 is a handle 208, a neck 210, and a fluid exit aperture 212 coupled to the neck 210. In one embodiment, dispenser 200 includes a filter 214 that is removably coupled in aperture 206.

Filter 214 is configured to remove infectious agents from the fluid provided to dispenser 200. Filter 214 can have any media for filtering fluid including but not limited to, ceramic, ceramic with carbon core, glass fiber, a structured matrix, and iodine resin. In the exemplary embodiment, filter 214 is manufactured with a pore size of 1 micron or smaller. Alternatively, filter 214 can have any pore size that facilitates sterilization as described herein. In some embodiments, filter 214 is fixedly coupled inside of dispenser 214. Filter 214 may have a UVC light source incorporated into the filter 214 to ensure dispenser 200 is sanitized.

In the exemplary embodiment, dispenser 200 includes a base 220. Coupled within base 220 is a UV light source 222. In some embodiments, an ultrasound transducer 224 is coupled within base 220. In some embodiments, light source 222 is an ultraviolet LED or LED array. Alternatively, light source 222 can be any light source that provides UVC waves, including but not limited to, a fluorescent UVC bulb and a laser. A light amplifying device may be adjacent the light source 222 to amplify its output. For example, the light from the light source 222 may be amplified by a Fresnel lens or other optic. Transducer 224 is configured to provide ultrasound to fluid retained in reservoir 204. In one embodiment, base 220 is sealed from fluid reservoir 204, such that fluid in reservoir 204 cannot contact light source 222 and/or transducer 224. Alternatively, base 220 is open to reservoir 204 to enable fluid in reservoir 204 to contact light source 222 and/or transducer 224.

In one embodiment, light source 222 and/or transducer 224 are powered and run by circuits (e.g. circuits 100, 110, 120, 130, and 140) coupled in base 220. In such an embodiment, a power source 226, including but not limited to, a battery, is the source of power. In an alternative embodiment, dispenser 200 is configured to have power received on a docking station 230. Docking station 230 includes a transmitter 232 for providing power to power source 226. In one embodiment, power is supplied from transmitter 232 to power source 226 wirelessly through induction. Alternatively, power can be supplied from transmitter 232 to power source 226 in any manner that facilitates power transfer.

Utilizing light source 222 and/or transducer enables dispenser 200 to sanitize fluid within the dispenser and/or the inner walls of the dispenser. Treating and/or sanitizing water prior to using dispenser 200 will reduce the risk of being infected with infectious agents (e.g. the PAM disease). In one embodiment, the fluid (e.g. water) is treated for a specified amount of time with the light source 222 before use of dispenser 200. In some embodiments, the fluid (e.g. water) is treated for a specified amount of time with ultrasound emitted from transducer 224 before use of dispenser 200. The treatment times of UV and/or ultrasound and the frequencies of the ultrasound can be specified to target a specific infectious agent. In one example, the light source 222 and the ultrasound transducer 224 may be operated simultaneously to disinfect the dispenser 200. Bubbles in the fluid caused by the ultrasound transducer 224 may assist disinfection by the light source 222. In another example, the light source 222 and the ultrasound transducer 224 may be used at different times, independent of one another. Additionally, the light source 222 could also be used to sanitize the dispenser 200 after each use. In some embodiments, one or more sensors 240 are positioned in dispenser 200 to monitor at least one of temperature, power, pH, and other parameters needed to determine if the UV and/or ultrasound is or has been effective in sterilizing the dispenser 200 and/or the fluid within the dispenser 200.

In one embodiment, an electrical current is transmitted to fluid in reservoir 204 to disrupt any infectious agents present in the fluid. In such and embodiment, positive and negative electrodes are integrated into reservoir 204 and/or base 220 and an electrical current is conducted through the fluid before use of dispenser 200. Dispenser 200 can be configured to supply either or both of AC and DC current to the fluid prior to use.

Figure 7:
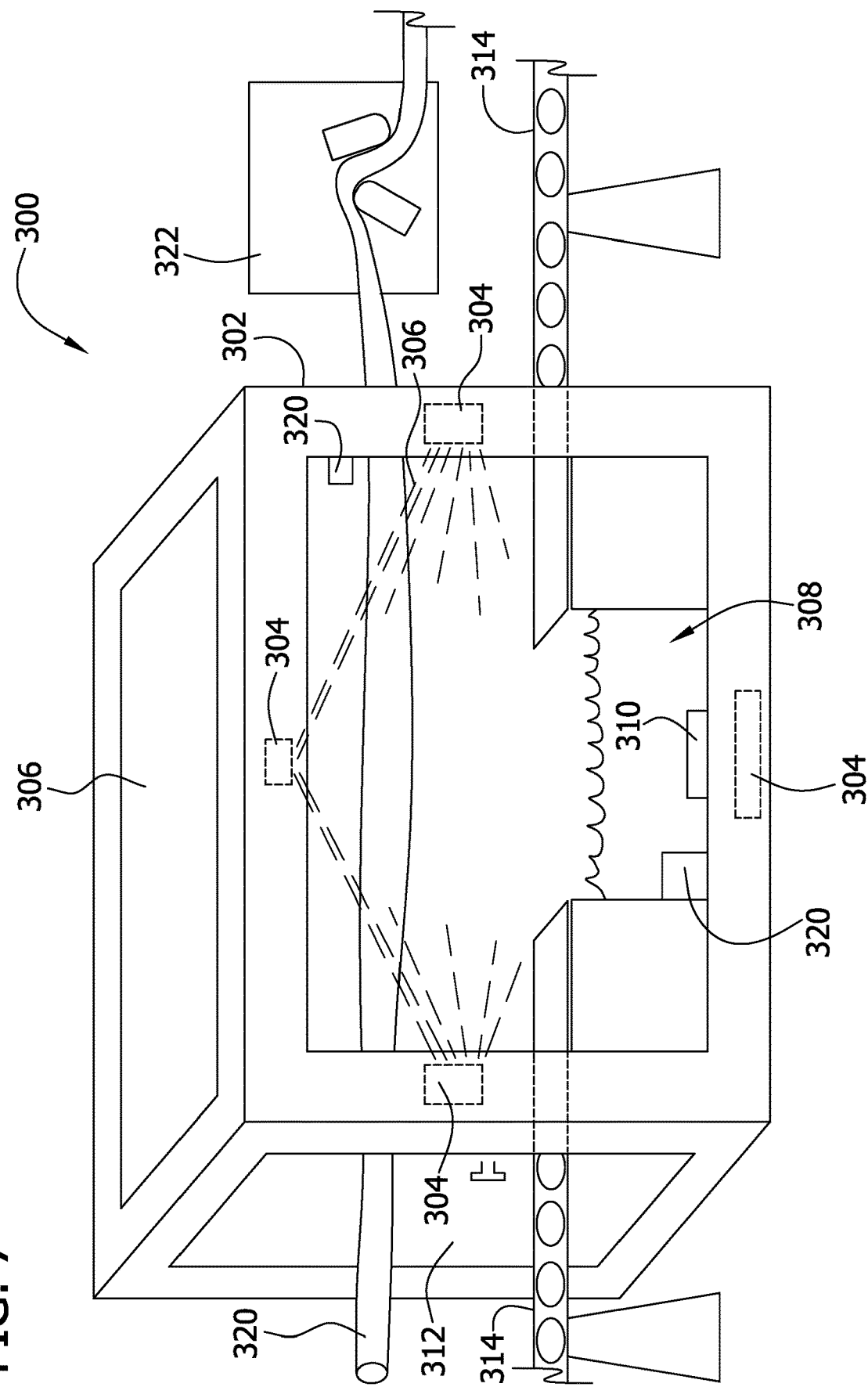
FIG. 7 is a perspective view of a device for at least one of disinfecting, sanitizing, and sterilizing an object for use with any combination of the circuits shown in FIGS. 1-5.

FIG. 7 is a perspective view of an object sanitizer 300 for use with any combination of circuits 100, 110, 120, 130, and 140 shown in FIGS. 1-5. In the exemplary embodiment, sanitizer 300 is configured to be located in a sterile environment (e.g. medical facility or food processing facility). Sanitizer 300 includes a housing 302 having one or more light sources 304 positioned in the housing. In some embodiments, light source 304 is an ultraviolet LED or LED array. Alternatively, light source 304 can be any light source that provides UVC waves, including but not limited to, a fluorescent UVC bulb and a laser. In one embodiment, light source 304 is configured to provide nutrients (e.g. vitamin D) to food placed in contact with the UV light emitted from light source 304.

Housing 302 also includes a viewable shield 306. Shield 306 is configured to protect users from UV light transmitted in housing 302. In some embodiments, shield 306 is a window that is polarized to allow a user to see into sanitizer 300 and not be exposed to UV light. Alternatively, shield may be have an opaqueness that blocks UV light while enabling a user to see objects placed in sanitizer 300. Shield 306 can be fabricated from any material capable of blocking UV light and permitting a user to see though the shield, including but not limited to glass and plastic.

In the exemplary embodiment, sanitizer 300 includes a bath 308 for retaining objects and fluid. In some embodiments, bath 308 includes a transducer 310 configured to provide ultrasound to fluid retained in bath 308. Transducer 310 is configured to provide vibratory energy (i.e. ultrasound) to the fluid in bath 308 to aid in dislodging and/or removing debris from objects placed in bath 308. For example, in a surgical setting, tissue and/or surgical debris that has attached to surgical instruments can be removed in a hands free manner. Likewise, in a food preparation setting, organic or inorganic material that has attached to food products can be removed from the food product by the vibratory energy transmitted through bath 308.

In some embodiments, sanitizer 300 includes a door 312 for inserting and removing objects subject to sterilization. In one embodiment, door 312 is also a shield 306. In some embodiments, a conveyer belt 314 is used in conjunction with sanitizer 300 to bring objects into and out of exposure with UV light transmitted by light source 304. Conveyer belt 314 can be configured to extend though bath 308, thus allowing objects placed on belt 314 to be exposed to ultrasound in a fluid environment. Alternatively, belt 314 can be configured to only provide UV light exposure to objects placed on belt 314. In some embodiments, one or more sensors 320 are positioned in sanitizer 300 to monitor at least one of temperature, power, pH, and other parameters needed to determine if the UV and/or ultrasound is or has been effective in sterilizing the sanitizer 300 and/or the fluid within the bath 308.

In one embodiment, sanitizer 300 is configured to sanitize fluid that is channeled through a tubular structure 320. In such an embodiment, tubular structure 320 can be coupled to a pump 322 configured to channel fluid through structure 320 and sanitizer 300. In one embodiment, the fluid channeled through structure 320 is blood extracted from a patient. This would enable blood to be sanitized and/or cleansed with UV and/or ultrasound. Such treatment would disrupt and/or kill infectious agents present in blood without killing red blood cells. In an alternative embodiment, sanitizer 300 can be utilized in conjunction with any hose system including, but not limited to, dialysis machines, heart-lung machines, coffee pots, humidifiers, jewelry cleaners, parts cleaners, foot baths, whirlpools, bath tubs, swimming pools, wax baths, pet food bowls, RV water tank, water heater, HVAC systems, refrigerators, dishwashers, as well as tanks and hoses in the fermentation of alcohol. As such, an ultrasonic signal could be transmitted through the lines that beer and fermented beverages are ran through in bars and restaurants to prevent the build-up biofilm and keep the lines clean by providing vibratory energy that would prevent blockage and preserve the beverage (e.g. preserve beverage integrity).

In the exemplary embodiment, fluid is channeled through sanitizer 300 by pump 322 at a time increment that will enable the fluid within structure 320 to be exposed to UV and/or ultrasound for a duration long enough to have a deleterious effect on infectious agents in the fluid. In some embodiments, the rate of speed of the fluid being channeled is selected based on the fluid flowing through structure 320. Alternatively, the rate of speed of the fluid being channeled is selected based on the infectious agent that is to be treated and/or eliminated such that the fluid is exposed to the UV and/or ultrasound for the predetermined time. The tubular structure 320 and/or the light source 304 may be movable (e.g., rotatable or oscillatable) to ensure the fluid in the tubular structure is exposed to the UV light from the light source as it flows through the tubular structure. In the same or another embodiment, the fluid in the tubular structure 320 may swirl around within the tubular structure. A device for causing swirling of the fluid flow in the tubular structure 320 may be provided.

Figure 8:
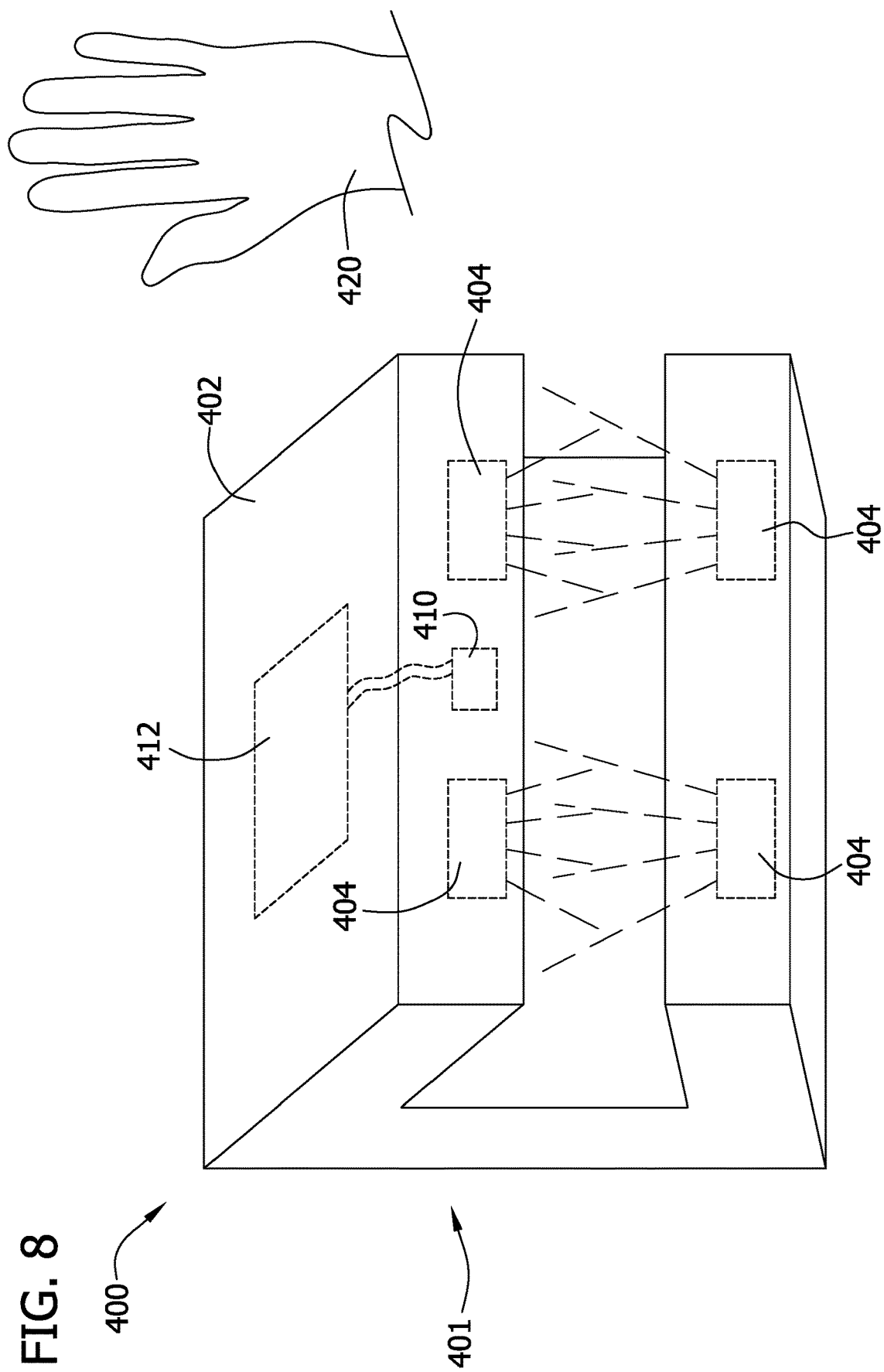
FIG. 8 is a perspective view of an exemplary device for at least one of disinfecting, sanitizing, and sterilizing a glove for use with any combination of the circuits shown in FIGS. 1-5.

FIG. 8 is a perspective view of an exemplary glove sanitizing system 400 for use with any combination of circuits 100, 110, 120, 130, and 140 shown in FIGS. 1-5. System 400 includes a glove sanitizer 401 having a housing 402 with one or more light sources 404 positioned in the housing. In some embodiments, light source 404 is an ultraviolet LED or LED array. Alternatively, light source 404 can be any light source that provides UVC waves, including but not limited to, a fluorescent UVC bulb and a laser.

In the exemplary embodiment, housing 402 includes an aperture 406 configured to enable a user wearing gloves to insert the gloves into housing 402 to enable exposure of the gloves to UV emitted by light source 404. The illustrated glove sanitizer 401 includes upper and lower UV light sources 404, whereby the users hands are positionable between the upper and lower light sources. The glove sanitizer 401 may be configured to activate the light sources 404 for a specified period of time (i.e., a timer) and/or communicate instructions to the user. A microprocessor may operate the glove sanitizer 401. In some embodiments, a sanitizing spray nozzle 410 is coupled in housing 402 to provide fluid disbursement to objects placed in glove sanitizer 401. In such an embodiment, nozzle 410 is coupled to a fluid reservoir 412 positioned in housing 402. Nozzle 410 is configured to provide a sanitizing agent to objects in glove sanitizer 401. In one embodiment, an alcohol based solution is ejected from nozzle 410. Alternatively, any sanitizing agent can be transmitted from nozzle 410 that facilitates sanitizing as described herein.

In the exemplary embodiment, system 400 includes a disposable glove 420 for use with glove sanitizer 401. Glove 420 can be manufactured from any suitable material including but not limited to, latex, nitrile rubber, vinyl, and neoprene. In some embodiments, glove 420 includes a coating to lubricate the gloves, making them easier to put on the hands. In the exemplary embodiment, glove 420 is fabricated to have an opaqueness that blocks UV light from being transmitted to the skin of a wearer. System 400 enables a user to sanitize a glove that would normally require disposal. For example, a medical professional could utilize 1 set of gloves 420 for examining different patients with the use of glove sanitizer 401 to sanitize the gloves between patients. Likewise, a user in a food processing facility would be able use 1 set of gloves between different foods with the use of glove sanitizer 401 to sanitize the gloves between work areas. System 400 provides cost effective way to prevent infectious agent transmission with a decrease in waste. Such a system would also enable health care professionals to potentially avoid the requirements of constant use of sterilizing agents on the skin. The glove sanitizer 401 may include a shield to inhibit a user's eyes from being exposed to UV light.

Figure 9:
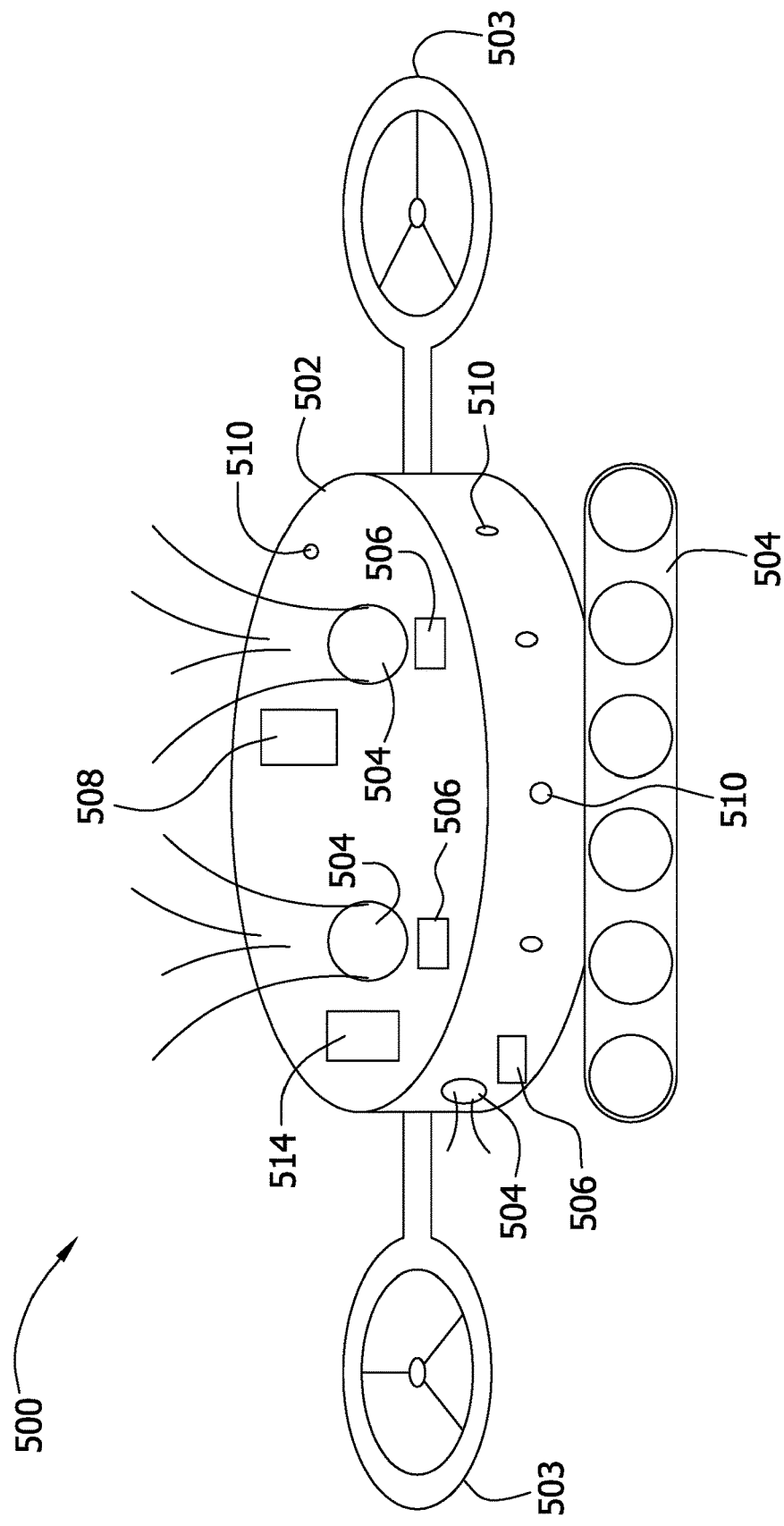
FIG. 9 is a perspective view of an exemplary robot for at least one of disinfecting, sanitizing, and sterilizing an object for use with any combination of the circuits shown in FIGS. 1-5.

FIG. 9 is a perspective view of an exemplary robot 500 for use with any combination of circuits 100, 110, 120, 130, and 140 shown in FIGS. 1-5. In the exemplary embodiment, robot 500 includes a housing 502 and a movement apparatus 504. In one embodiment, movement apparatus 504 is a continuous track that enables robot 500 to traverse over different terrain throughout a room. In an alternative embodiment, movement apparatus 504 includes at least one blade assembly 503 to enable robot 500 to fly. Alternatively, movement apparatus 504 can be any apparatus that enables movement of robot 500 including, but not limited to wheels and an air/fluid bladder (e.g. hovercraft).

Coupled to housing 502 is a plurality of light sources 504. Light sources 504 can be positioned in any location on housing including, but not limited to, a top surface, a bottom surface, and side panels. In some embodiments, light source 504 is an ultraviolet LED or LED array. Alternatively, light source 504 can be any light source that provides UVC waves, including but not limited to, a fluorescent UVC bulb and a laser. In one embodiment, light source 504 is associated with an image capturing device 506. Image capturing device 506 is configured to capture images, either continuously or intermittently, to monitor what surfaces have come in contact with UV emitted by light source 504. Image capturing device, can be any image detection device including, but not limited to, a camera, video camera, machine vision, and/or laser. In one embodiment, the captured images are compared with images of a room, either received from another computing device (e.g. smartphone, tablet, laptop, or PC) or from a separate capturing device 508 located on housing 502 to determine what has come in contact with UV and the duration of the contact.

In the exemplary embodiment, robot 500 includes a plurality of sensors 510 coupled to housing 502. Sensors 510 can be configured to track and provide visual information that will be utilized by a processor in housing 502 to steer robot 500. Additionally, sensors 510 can be configured to monitor at least one of temperature, power, pH, and other parameters needed to determine if the UV is or has been effective in sterilizing a room.

In one embodiment, robot 500 includes a suction (vacuum) port, fabric attachment pad, and a spray nozzle coupled to the bottom surface of housing 502. The suction port, fabric attachment pad, and spray nozzle, along with a light source 504, enable robot 500 to clean and sanitize floors. In one embodiment, robot 500 includes an attachment port 514 that is configured to receive a handle that would enable a user to manually move robot 500.

Figure 10:
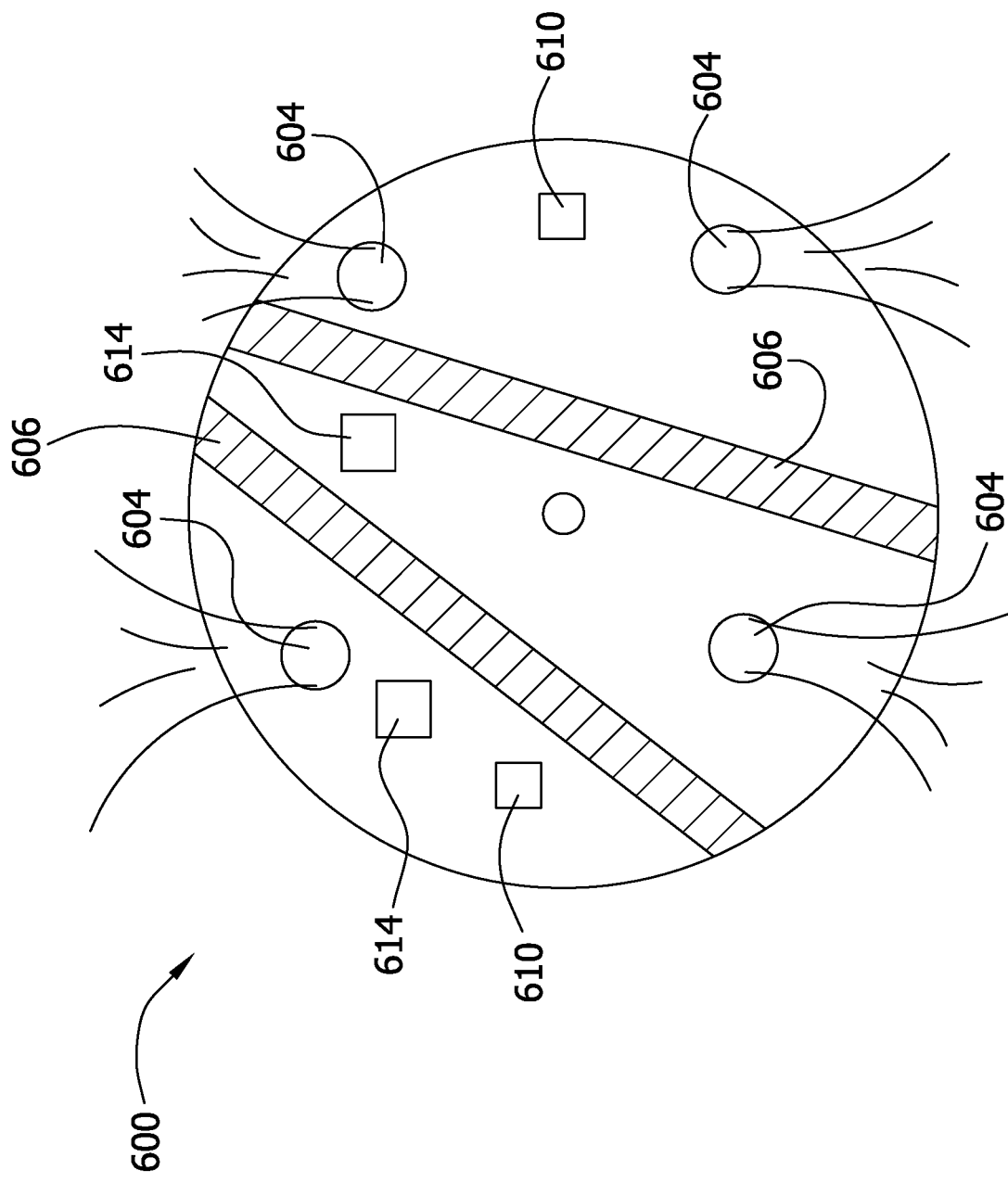
FIG. 10 is a perspective view of a portable device for at least one of disinfecting, sanitizing, and sterilizing an object for use with any combination of the circuits shown in FIGS. 1-5.

FIG. 10 is a perspective view of a portable sanitizer 600 for use with any combination of circuits 100, 110, 120, 130, and 140 shown in FIGS. 1-5. In the exemplary embodiment, sanitizer 600 includes a circular housing 602 that enables sanitizer to move over varied terrain. Alternatively, housing 602 can have any shaped structure that enables movement, including but not limited to oval. Coupled to sanitizer 600 is a plurality of light sources 604. In some embodiments, light source 604 is an ultraviolet LED or LED array. Alternatively, light source 604 can be any light source that provides UVC waves, including but not limited to, a fluorescent UVC bulb and a laser. In some embodiments, one or more tracks 606 are coupled around and/or on housing 602. Tracks 606 can be configured to move constantly and/or intermittently based on a desired effect. Tracks 606 also enable sanitizer 600 to move in various movements that provide UV from different angles to provide maximum exposure to objects.

In one embodiment, sanitizer 600 includes sensor(s) 610. Sensor 610 can be configured to monitor at least one of temperature, power, pH, and other parameters needed to determine if the UV is or has been effective in sterilizing a room. In one embodiment, sensor 610 is configured to receive monitor visible light. When visible light is not present (e.g. environment is dark) sensor 610 transmits a signal to a processor positioned in housing 602 and/or light source 604 that will initiate a UV sequence that will transmit UV light. Sanitizer 600 is effective at preventing and/or killing infectious agents on food items in a refrigerator, drawer, cabinet, and/or any other dark space while preventing UV exposure to users. In some embodiments, sanitizer 600 is moisture sealed and configured to be placed in a dishwasher and/or clothes washing machine to sanitize objects in the washer. In one embodiment, a transducer 614 is coupled to housing 602 to emit ultrasound.

Figure 11:
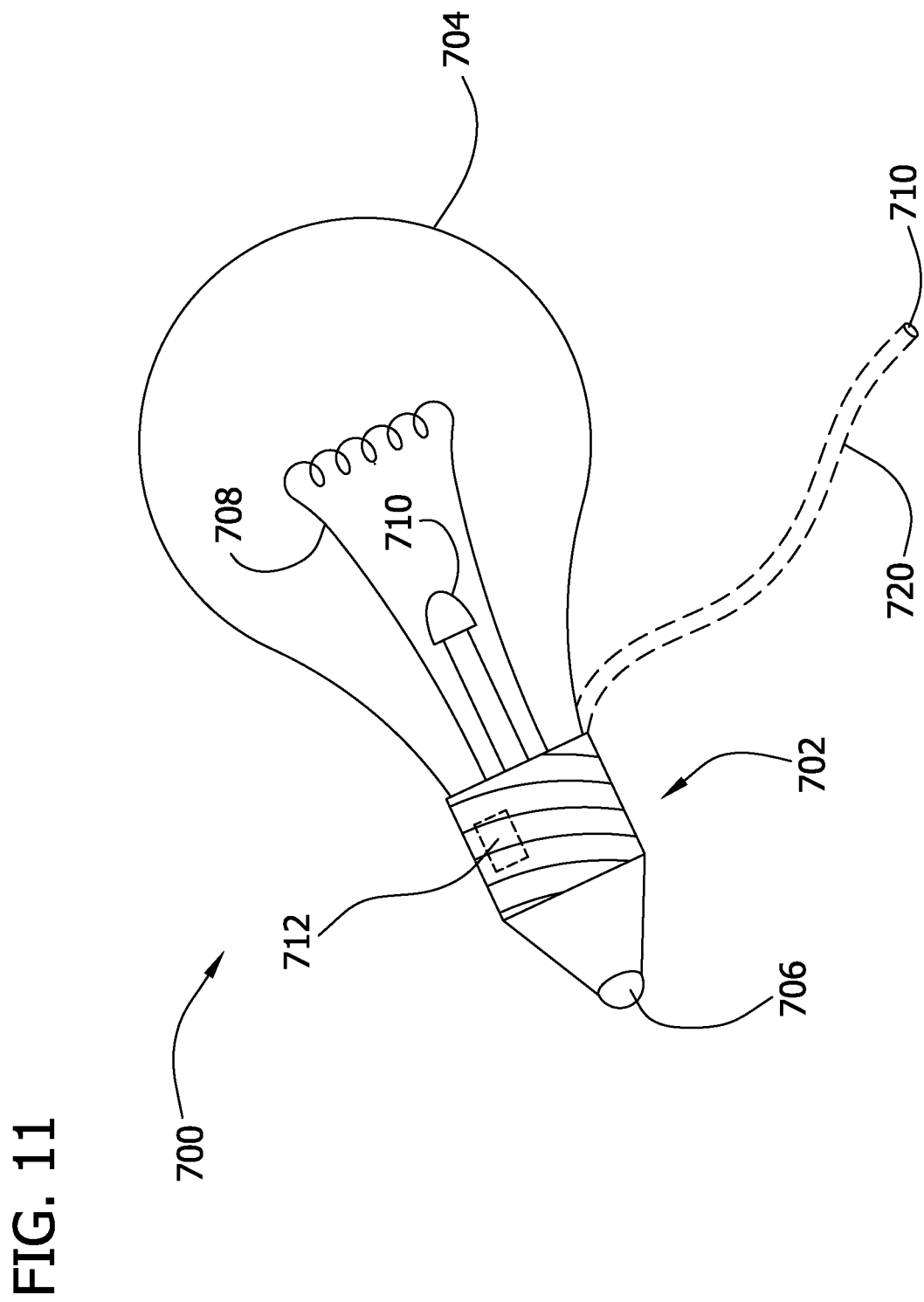
FIG. 11 is a perspective view of a dual source light for use with any combination of the circuits shown in FIGS. 1-5.

FIG. 11 is a perspective view of a dual source light 700 for use with any combination of circuits 100, 110, 120, 130, and 140 shown in FIGS. 1-5. In the exemplary embodiment, light 700 includes a base 702 and a bulb or tube 704 coupled to the base 702. Tube 704 can be fabricated from any material that is capable of retaining gas without leaks including but not limited to, glass and plastic. Base 702 includes an electrical contact 706 and a ballast for converting and/or limiting current in light 700. The ballast can be magnetic or electronic. Light 700 also includes a first light source 708 positioned in tube 704 and coupled to the ballast. First light source 708 can be any light source that provides visible light including, but not limited to incandescent, fluorescent, and halogen.

In the exemplary embodiment, light 700 includes a second light source 710 configured to provide UVC. In some embodiments, second light source 222 is ultraviolet LED or LED array. Alternatively, light source 222 can be any light source that provides UVC waves, including but not limited to, a fluorescent UVC bulb and a laser. In one embodiment, second light source 222 is coupled to a second light power source 712 positioned in base 702. Power source 712 is configured to receive and store current flowing into and/or through contact 706 and/or the ballast including but not limited to a super-cap and a battery.

In operation, when power is supplied to light 700, first light source 708 is powered from the current supplied and the second light power source 712 is charged. When power to light 700 is stopped, second light source 710 is powered by power source 712. For example, if light 700 were placed inside a refrigerator, when a door to the refrigerator opened, first light source 708 would illuminate the inside of the refrigerator and when the door closed, UVC would be provided to the inside of the refrigerator to sterilize food items and/or the refrigerator itself.

It should be noted that light 700 could be connected to a sensor that would provide signals for providing and eliminating UVC light. For example, light 700 could be configured to be placed above kitchen counters and only emit UVC when no motion is detected by one or more motion detection sensors. Additionally, second light source 708 can be on a flexible line 720 coupled to light 700 that enables a user to position and/or direct the UVC to a desired location.

Figure 12:
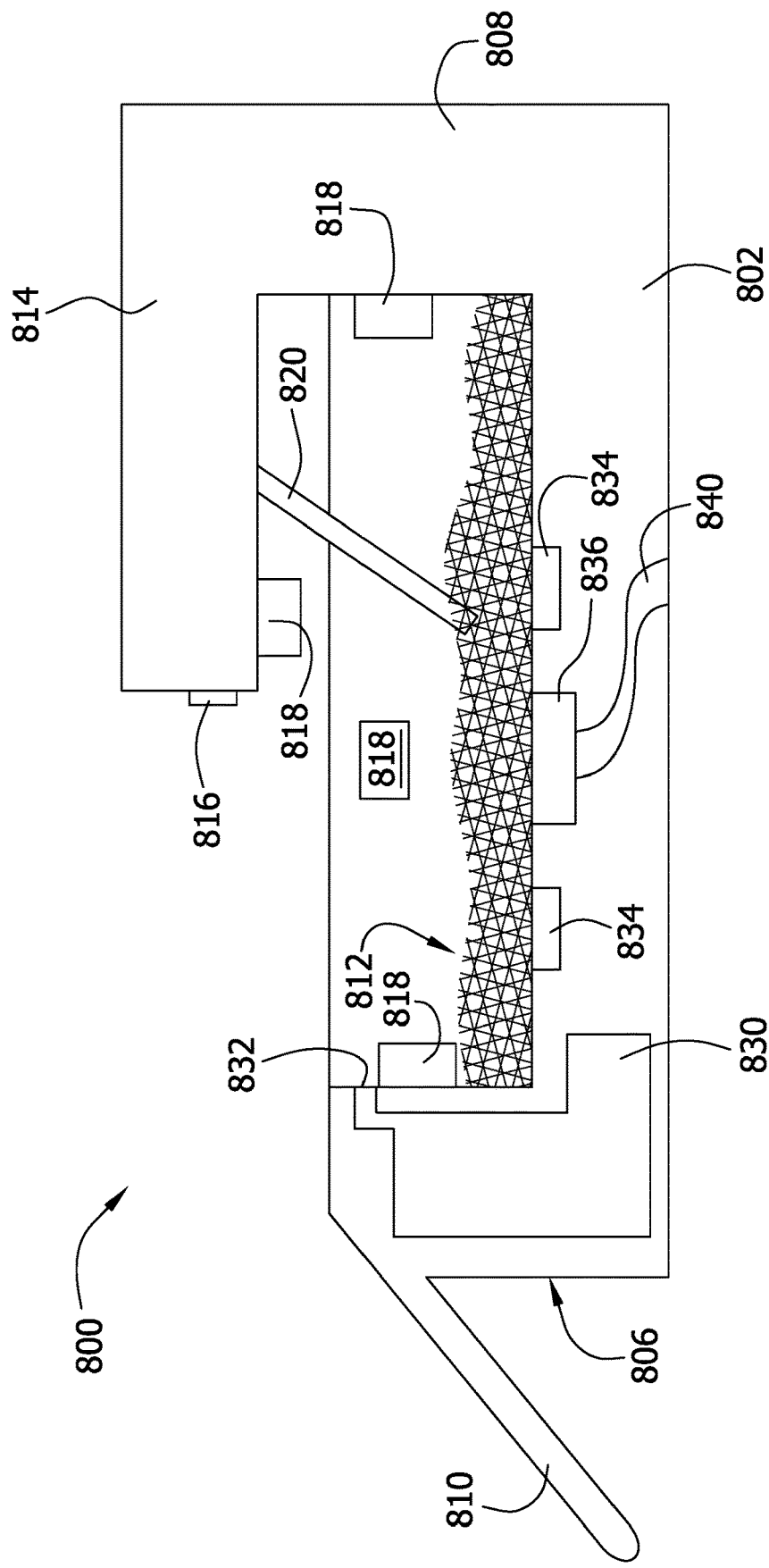
FIG. 12 is a side cut-away view of an exemplary litter box for use with any combination of the circuits shown in FIGS. 1-5.

FIG. 12 is a side cut-away view of an exemplary litter box 800 for use with any combination of circuits 100, 110, 120, 130, and 140 shown in FIGS. 1-5. Box 800 includes a base 802, side panels 804, a front lip 806, and a back support 808. In some embodiments, a ramp 810 is coupled to lip 806 to provide an animal entry and exit into box 800. Litter media 812 is placed on base 802 and retained in place by panels 804, lip 806, and support 808.

Support 808 includes an overhang 814 that is substantially parallel to base 802. In the exemplary embodiment, coupled to overhang is a motion sensor 816 configured to detect when an animal is or has been in box 800. At least one light source 818 is coupled in box 800 to provide UVC to media 812 and/or excrement left in box 800. In one embodiment, a rake is coupled to overhang 814.

In operation, when sensor 816 detects an animal has entered and exited box 800, a signal is transmitted to light source(s) 818 to transmit UVC, for a predetermined time to sanitize media 812 and/or excrement left in box 800. In one embodiment, a signal is also transmitted to rake 820 to scoop and/or rake media 812 for disposal purposes.

In some embodiments, box 800 is filled with fluid (e.g. water or sterilized fluid) to clean box after an animal has entered and exited box 800. In such an embodiment, fluid is provided to box 800 through a plumbing source 830 and fluid aperture 832. One or more transducers 834 are coupled to base 802 to provide vibratory energy (i.e. ultrasound) to fluid filled in box 800. After ultrasound is transmitted to the fluid by transducers 834 for a predetermined amount of time, the fluid is drained through drain 836 and/or line 840.

The UVC and ultrasound provided to box 800 is configured to treat and/or eliminate Toxoplasma gondii in the excrement, which is linked to toxoplasmosis. For example, the UVC may damage DNA/RNA of the Toxoplasma gondii, and the ultrasound may break up the cell wall membrane and spore wall. Additionally, the vibratory energy provided by the ultrasound from transducers 834 can break down the excrement and the Toxoplasma Gondii in the excrement.

Figure 13:
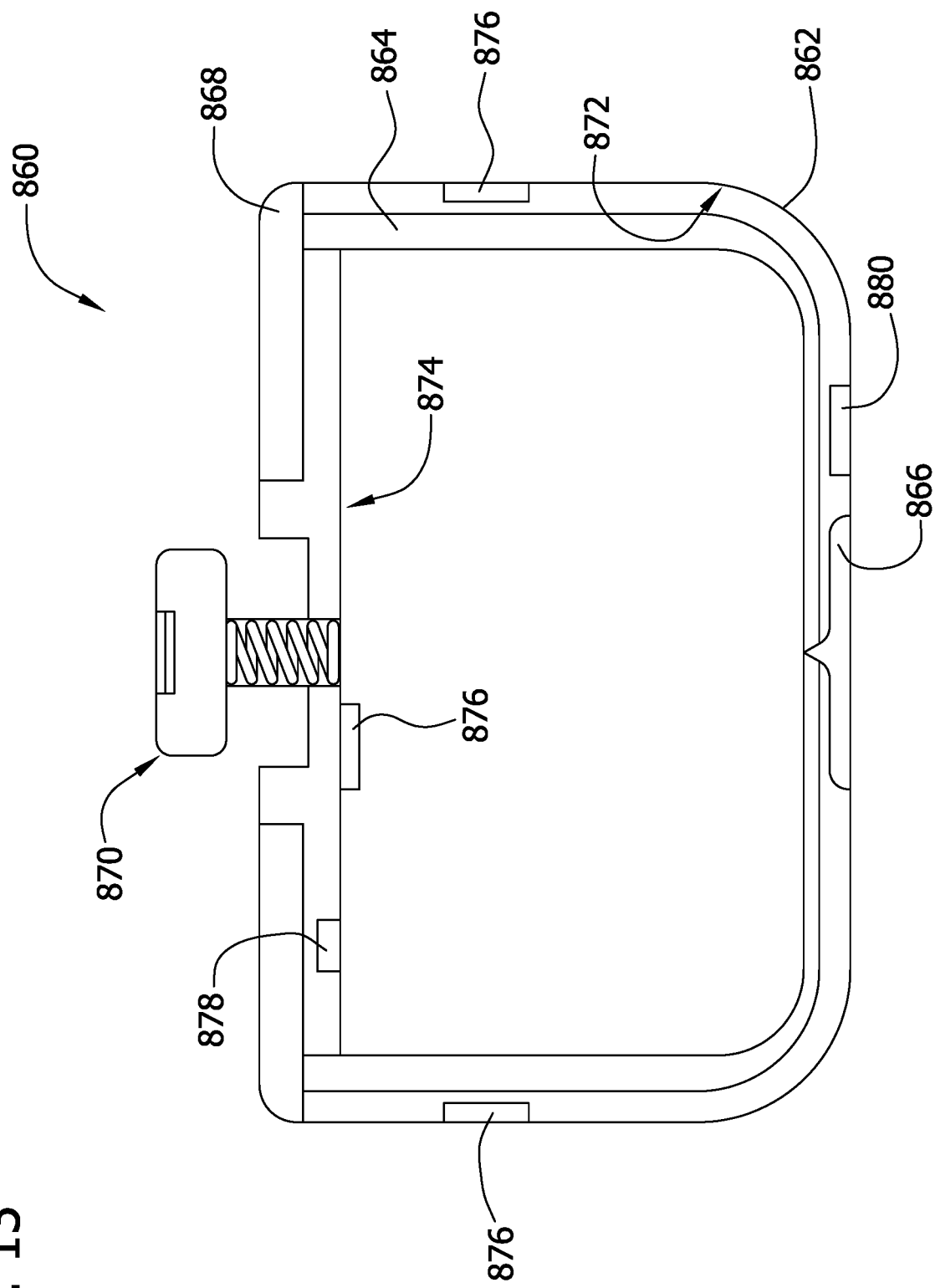
FIG. 13 is a side cut-away view of a device for at least one of disinfecting, sanitizing, and sterilizing food for use with any combination of the circuits shown in FIGS. 1-5.

FIG. 13 is a side cut-away view of a food sterilization device 860 for use with any combination of circuits 100, 110, 120, 130, and 140 shown in FIGS. 1-5. In the exemplary embodiment, device 860 is configured to wash and/or air dry food items through rotational energy. Device 860 includes an outer bowl 862 configured to block UVC, an inner bowl 864 that is configured to be positioned on a pivot point 866 of outer bowl 862. Device 860 also includes a lid 868 configured to removably couple to outer bowl 862 and block UVC. Lid 868 includes a spinner 890 that rotates inner bowl 864 with respect to out outer bowl 862. In the exemplary embodiment, spinner 890 is a pusher with an integrated spring. Alternatively, spinner 890 can be any device that provides rotation to inner bowl 864 including, but not limited to, a crank.

Coupled to an inner wall 872 of outer bowl 862 and/or underside 874 of lid 868 is a light source 876 configured to provide UVC to objects placed in inner bowl 864 and/or outer bowl 862. In one embodiment, light source 876 is ultraviolet LED or LED array. Alternatively, light source 876 can be any light source that provides UVC waves, including but not limited to, a fluorescent UVC bulb and a laser. In one embodiment, light source 876 is powered by a battery positioned in lid 868. Alternatively, light source 876 can be powered by any power source including but not limited to a solar panel and mechanical energy created from use of spinner 870.

In one embodiment, a transducer 880 is coupled to base 802 to provide vibratory energy (i.e. ultrasound) to fluid filled in outer bowl 862. The ultrasound provided by transducer 880 would be beneficial in not only eliminating infectious agents but also removing debris often found on food (e.g. mushrooms and lettuce).

Figure 14:
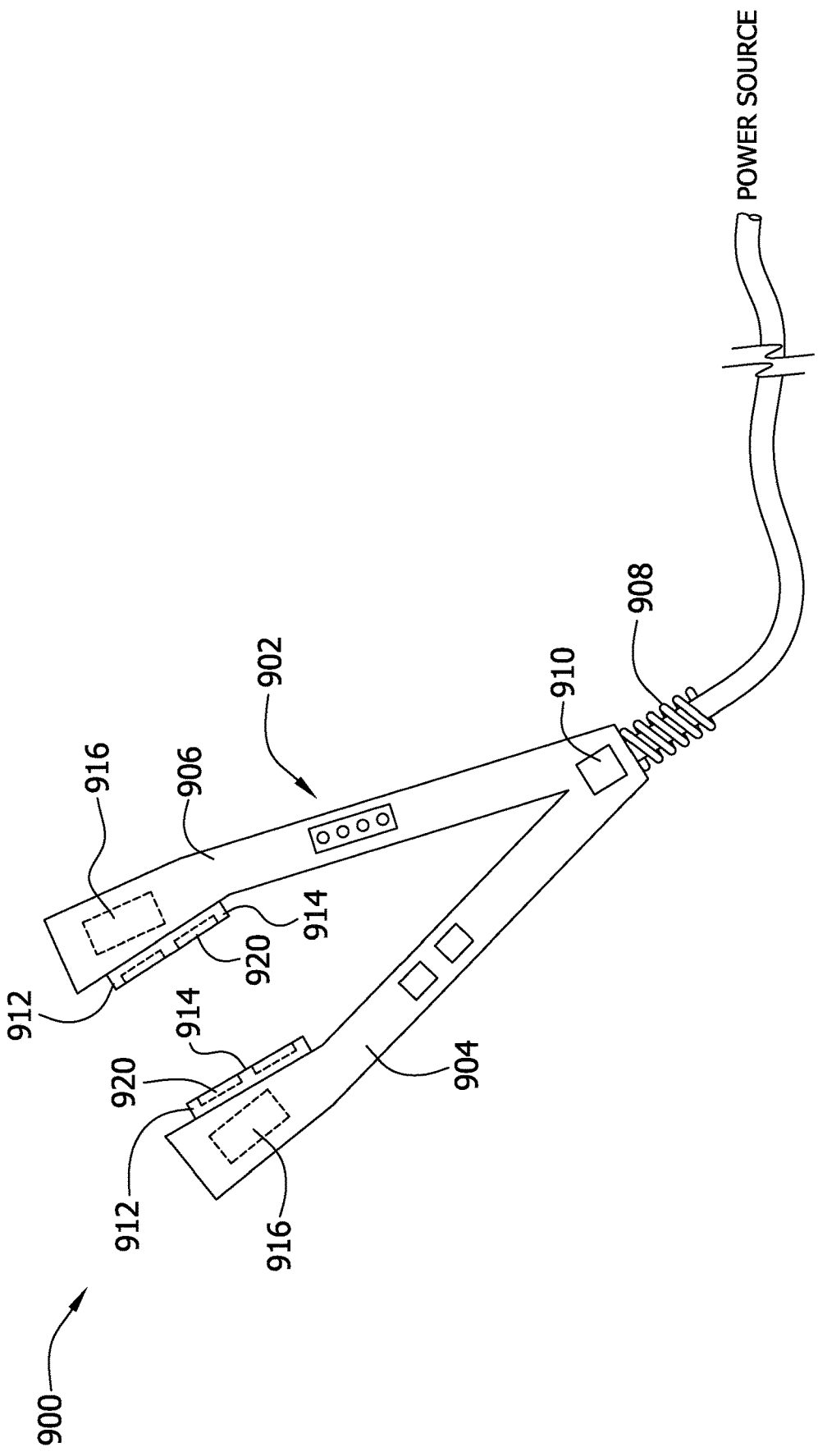
FIG. 14 is a perspective view of an exemplary hair device for use with any combination of the circuits shown in FIGS. 1-5.

FIG. 14 is a perspective view of an exemplary hair device 900 for use with any combination of circuits 100, 110, 120, 130, and 140 shown in FIGS. 1-5. Device 900 includes a hinged housing 902 having a first arm 904 and a second arm 906. Coupled to housing 902 is a power source 908 configured to provide power from a AC power source (e.g. wall outlet). Alternatively, a battery 910 is positioned in housing 902 and configured to charge via power source 908. Coupled to first arm 904 and second arm 906 are setting elements 912. In one embodiment, elements 912 are configured to heat to set hair in a particular position and/or location. Elements 912 can be fabricated from any material that is configured to retain heat including, but not limited to, aluminum, Teflon, ceramic, tourmaline, metal, and titanium. In some embodiments, elements 912 have a mating surface 914 that is substantially flat. Alternatively, mating surface 914 can have any shape that facilitates setting hair as described herein including, but not limited to, curved (for curls) and waved (for crimps). In one embodiment, transducers 916 are positioned within first and second arms 904 and 906 to provide vibratory energy that heats elements 912 to a desired temperature.

In the exemplary embodiment, a light source 920 is positioned in element 912. Light source 920 is configured to provide UVC to hair follicles. The UVC is emitted for a predetermined amount of time to achieve a desired result. For example, UVC treatment times are provided that enable enough UVC exposure to the hair follicles to at least one of cure hair dye placed on hair, change hair gloss, increase hair growth, and change hair sheen.

Figure 15:
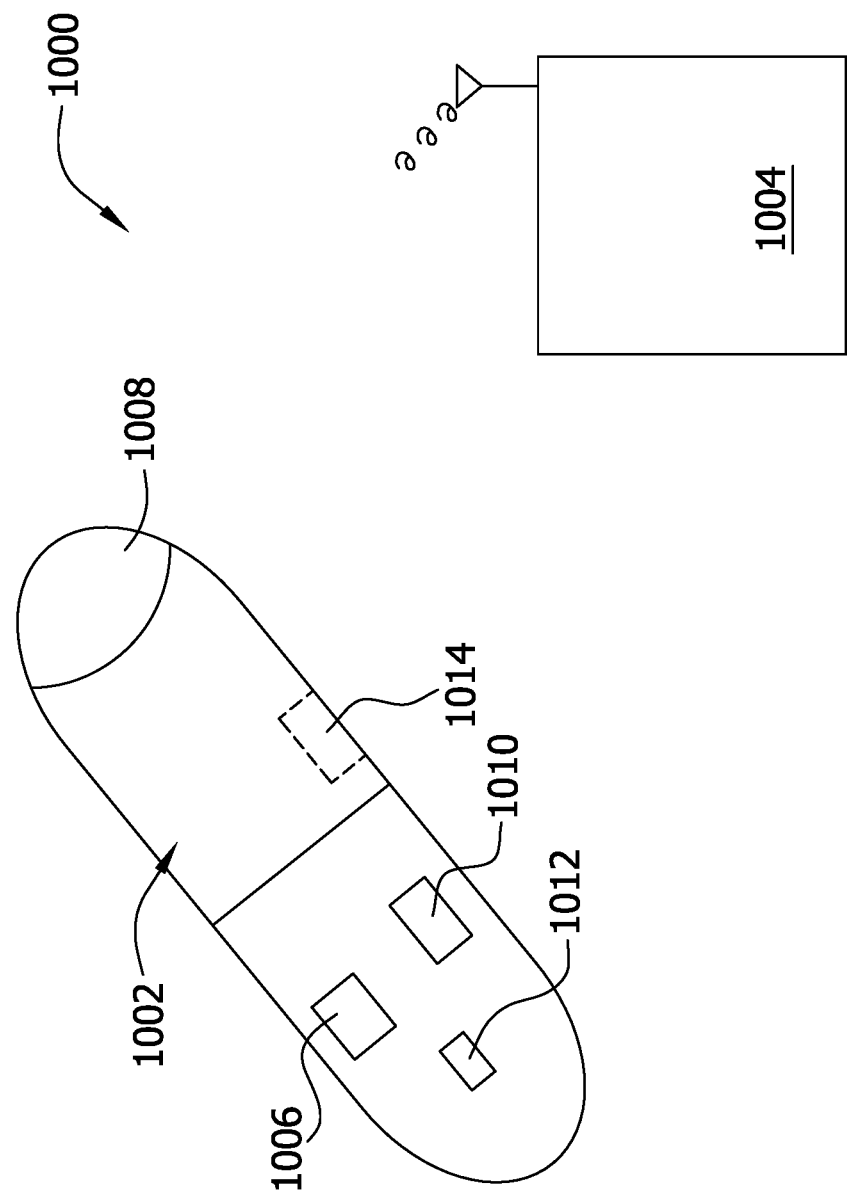
FIG. 15 is a schematic view of an exemplary pill system for use with any combination of the circuits shown in FIGS. 1-5.

FIG. 15 is a schematic view of an exemplary pill system 1000 for use with any combination of circuits 100, 110, 120, 130, and 140 shown in FIGS. 1-5. System 1000 includes a pill 1002 and a remote device 1004. In the exemplary embodiment, pill 1002 is ingested (i.e. swallowed) by a patient. Alternatively, pill 1002 is configured to be implanted in the body. Pill 1002 is sealed by a capsule having a power source 1006 that is coupled to a light source 1008. In one embodiment, light source 1008 is an ultraviolet LED, an LED array, or laser. Alternatively, light source 1008 can be any light source that provides UVC waves, including but not limited to, a fluorescent UVC bulb.

In one embodiment, pill 1002 includes a communication interface 1010 communicatively coupled to a processor 1012 and configured to send and receive signals with remote device 1004. In one embodiment, communication interface 1010 is configured to receive dosage information from remote device 1004. As such, remote device 1004 is configured to provide signals to pill 1002 and/or processor 1012 that instruct light source 1008 to provide UV and for what duration. Accordingly, pill 1002 is configured to provide feedback information to remote device 1004 via communication interface 1010. The feedback can include any information relating to pill 1002 including but not limited to, position information and applied dosage information. In one embodiment, pill 1002 includes a magnet 1014 that enables pill to be moved, positioned, and/or guided with the use of another magnet located outside the body. It should be noted that pill 1002 can be fabricated as a substantially flat strip that could be configured to be secured inside a vein and/or artery with any securement mechanism including, but not limited to, surgical glue and sutures. Additionally, pill 1002 can be fabricated to be partially or completely biodegradable within the body.

In one embodiment, remote device 1004 is a handheld device (e.g. smartphone, tablet, laptop, or PC) that is configured to receive, processor, store, and/or transmit information received from pill 1002. Alternatively, remote device 1004 can be a wearable device (e.g. patch) that is configured to receive information from pill 1002 and store and/or transmit the received information to another remote device (e.g. smartphone, tablet, laptop, or PC) for processing. If wearable device stores the information received, the wearable device can be communicatively coupled to a remote device for transmission of the data. It should be noted that circuits 100, 110, 120, and/or 130 are positioned in pill 1002 to work with light source 1008.

Figure 16:
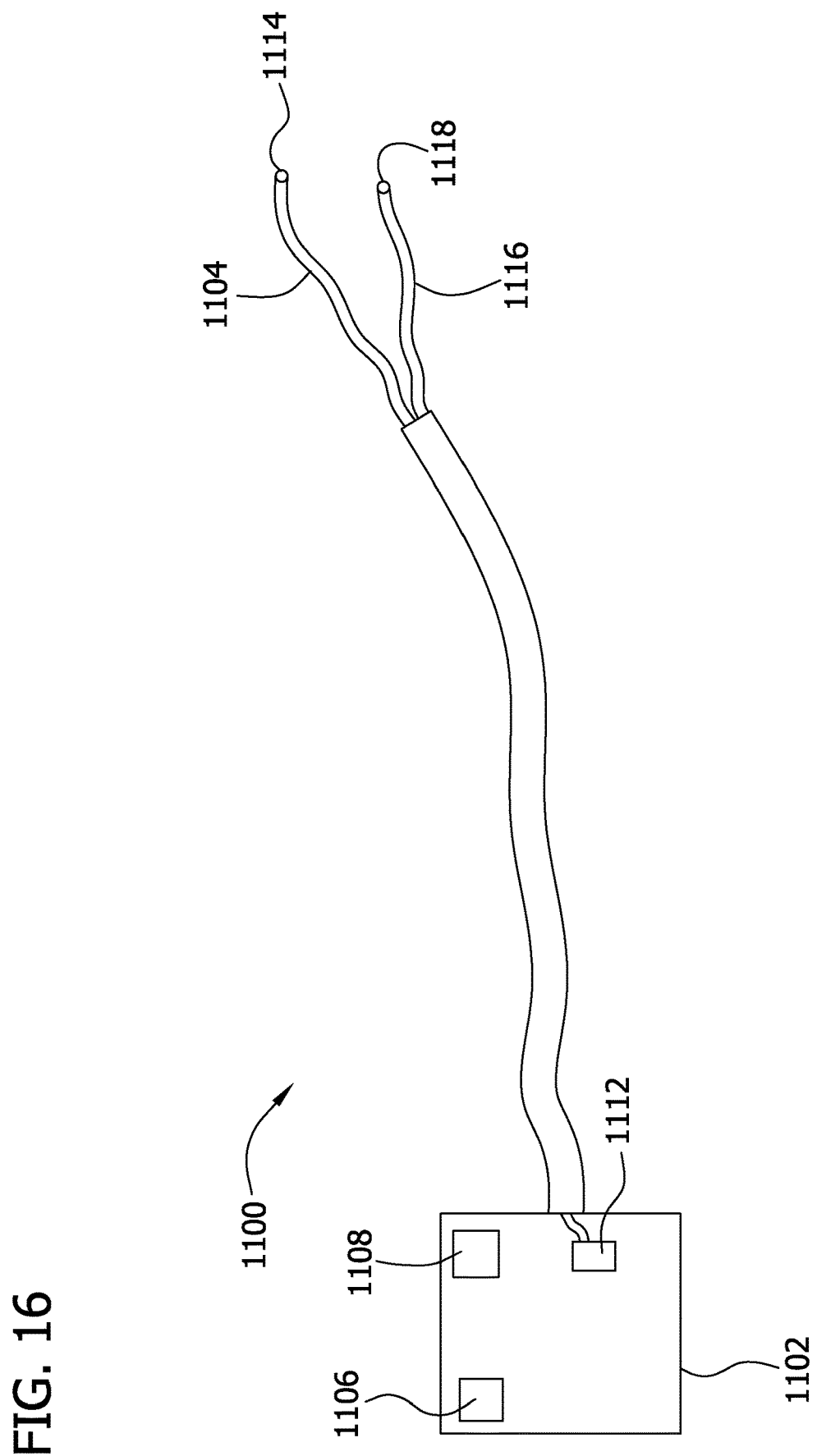
FIG. 16 is a schematic view of an exemplary catheter for use with any combination of the circuits shown in FIGS. 1-5 and the system shown in FIG. 15.

FIG. 16 is a schematic view of an exemplary catheter 1100 for use with any combination of circuits 100, 110, 120, 130, and 140 shown in FIGS. 1-5 and system 1000 shown in FIG. 15. Catheter 1100 is fabricated from a flexible material and configured to be inserted into veins and/or arteries. Catheter 1100 includes a base 1102 and a light lumen 1104 coupled to the base 1102. Base 1102 houses a processor 1106 that is communicatively coupled to a communications interface 1108 that is configured to send and receive signals with a remote device, such as device 1004 shown in FIG. 15.

In the exemplary embodiment, a light source 1112 is positioned in base 1102 and configured to provide UVC. Light source 1112 is coupled to light lumen 1104 to create a light pipe that emits UVC from a light aperture 1114 at a distal end of light lumen 1104. In one embodiment, catheter 1100 includes an ultrasound lumen 1116 that is configured to transmit ultrasound through a transducer 1118 positioned at a distal end of ultrasound lumen 1116. Additionally, circuits 100, 110, 120, 130, and/or 140 are positioned in housing 1102 to operate components 1112 and/or 1118. In some embodiments, a sensor is coupled to catheter 1102 to provide positional and/or environmental information (e.g. pH and temperature). In one embodiment, a balloon is coupled to the distal end of light lumen 1104. The balloon is transparent and configured to inflate and provide UVC an enlarged area as opposed to a focused beam.

Figure 17:
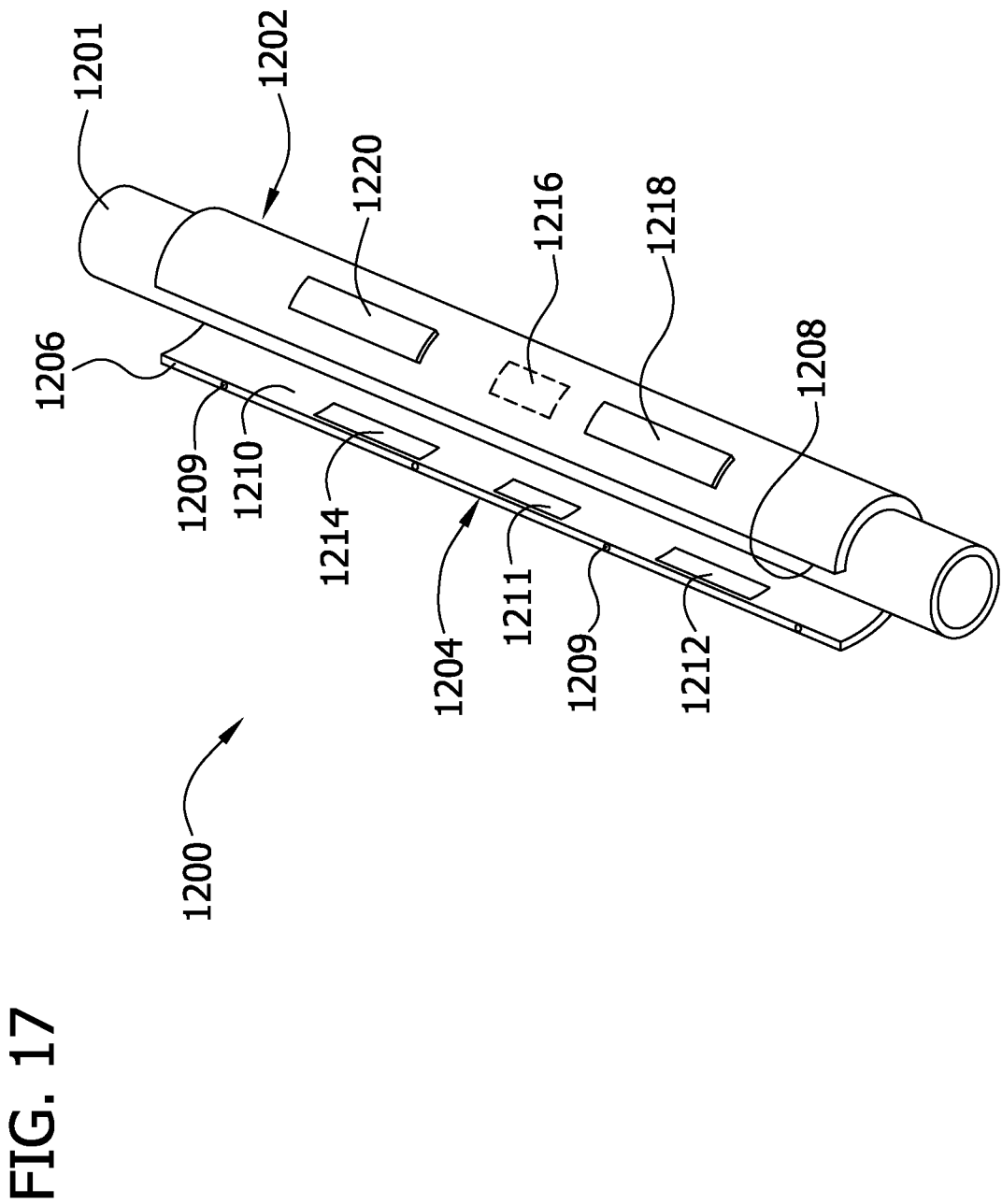
FIG. 17 is a perspective view of an exemplary sleeve for use with any combination of the circuits shown in FIGS. 1-5 and the system shown in FIG. 15.

FIG. 17 is a perspective view of an exemplary sleeve 1200 for use with any combination of circuits 100, 110, 120, 130, and 140 shown in FIGS. 1-5 and system 1000 shown in FIG. 15. Sleeve 1200 is configured to substantially encapsulate a portion of a vein and/or artery 1201. In the exemplary embodiment, sleeve 1200 is formed from a sterile material and includes a substantially rigid portion 1202 and a substantially flexible portion 1204. In one embodiment, sleeve is fabricated from a polymeric material. Alternatively, sleeve 1200 can be fabricated from any sterilizable material including, but not limited to, a collagen mesh and a scaffold. Flexible portion 1204 includes a flexible mating surface 1206 that mates with a rigid mating surface 1208 to form a substantially cylindrical shape to fit around vein and/or artery 1201. When closed, sleeve 1200 has an inner diameter that can be sized to friction fit around a particular vein or artery. For example, a sleeve configured to substantially encapsulate a portion of a vein in the arm adjacent the skin can have an inner diameter that is smaller than an inner diameter for a sleeve configured to substantially encapsulate an artery in the chest. In the exemplary embodiment, flexible portion 1204 is configured to be resilient such that mating surface 1206 is configured to spring back or return to mate with surface 1208 when moved. In another embodiment, the sleeve 1200 may include nitinol or other shape memory material, such that the sleeve takes on a smaller shape to encapsulating a portion of a vein or other blood vessel when implanted in the body due to the body temperature of the subject. In another example, a vacuum may be used to decrease the size of the sleeve 1200 so that the sleeve encapsulates the portion of a vein or other blood vessel. In one embodiment, a securement device 1209 is coupled to surfaces 1206 and 1208 to ensure closure of sleeve 1200. Securement device can be any coupling device including, but not limited to, magnets, suction device and locking device including nitinol.

In the exemplary embodiment, coupled to an inner surface 1210 of sleeve 1200 is a light source 1212 that is configured to provide UVC. In the exemplary embodiment, light source 1212 is an ultraviolet LED, an LED array, or laser. Alternatively, light source 1202 can be any light source that provides UVC. In some embodiments, a transducer 1214 is coupled to inner surface 1210 of sleeve 1200 to provide ultrasound to vein and/or artery 1201. In one embodiment, a magnet 1211 is coupled to inner surface 1210 of sleeve 1200. Magnet 1211 can be configured to change a flow and/or speed of blood moving through vein and/or artery 1201 by attracting and/or repelling iron particles in hemoglobin. In some embodiments, the power and/or attraction of magnet 1211 can be changed by a magnet outside the body, and/or a remote device.

Coupled to sleeve 1200 is a processor 1216 and power source (e.g. battery) that is communicatively coupled to a communications interface 1218 that is configured to send and receive signals with a remote device, such as device 1004 shown in FIG. 15. In some embodiments, a sensor 1220 is coupled to sleeve 1200 to provide positional and/or environmental information (e.g. pH and temperature).

In operation devices 1000, 1100, and 1200, shown in FIGS. 15-17 are configured to treat localized infections and/or cancer cells. The application of UVC and/or ultrasound damages DNA and/or RNA of cells. As such, replication of cancer cells can be retarded or stopped. Additionally, the powering of light sources 1008, 1112, 1210 and/or transducers 1118 and 1214 can be determined to power and emit energy in accordance with a dosimetry plan to ensure that a treatment site receives maximum UVC and/or ultrasound exposure while preventing complete degradation of surrounding tissue and/or organs.

In one embodiment, communication interfaces of devices 1000, 1100, and 1200 are configured to receive dosage information from the remote device. As such, the remote device is configured to provide signals to devices 1000, 1100, and 1200 that provide dosage information of UV and/or ultrasound. Accordingly, devices 1000, 1100, and 1200 are also configured to provide feedback information to the remote device via the communication interface. The feedback can include any information relating to devices 1000, 1100, and 1200 including but not limited to, position information, applied dosage information, and cellular health information.

Figure 18:
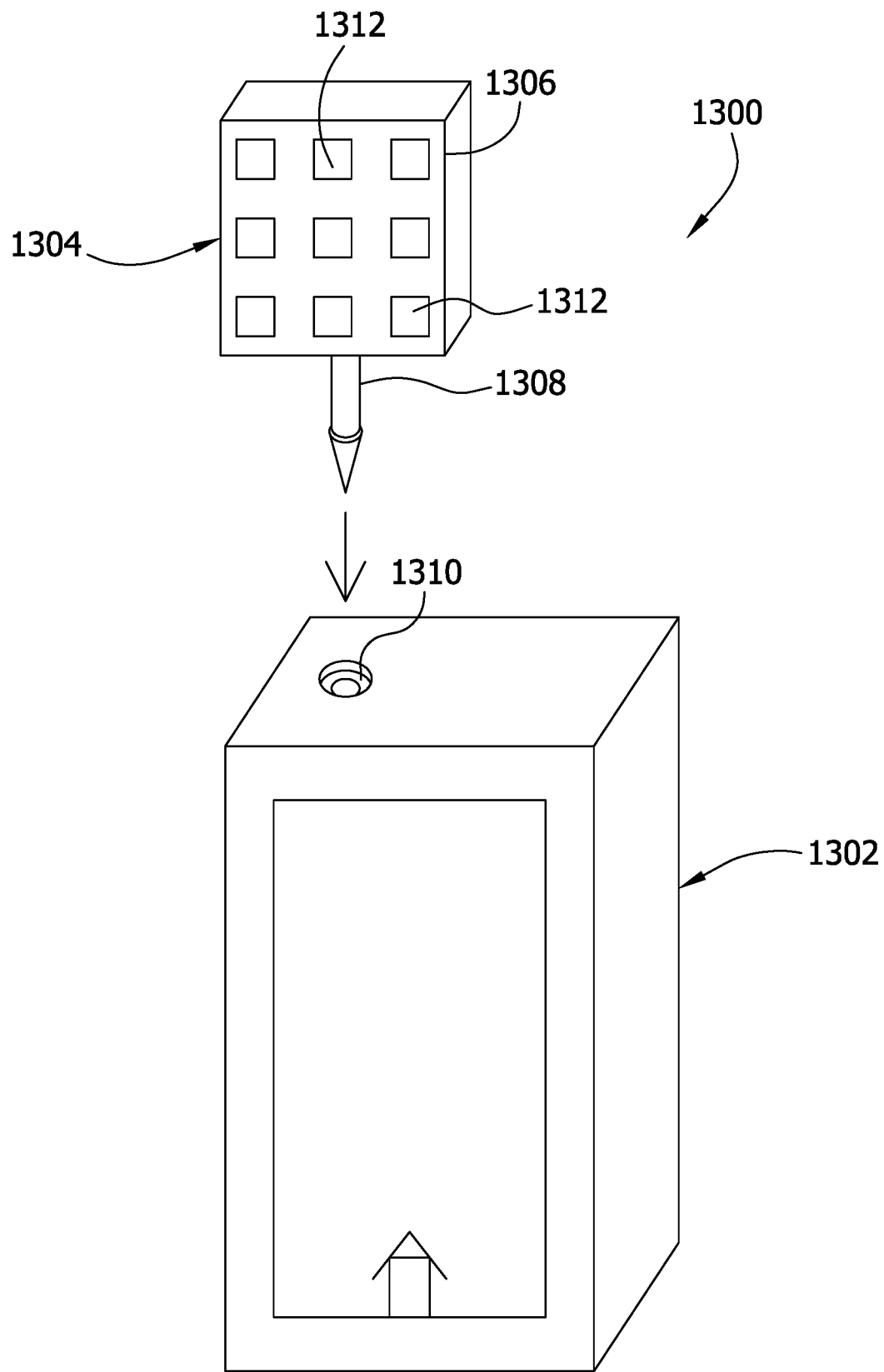
FIG. 18 is a perspective view of an exemplary portable system for at least one of disinfecting, sanitizing, and sterilizing an object for use with any combination of the circuits shown in FIGS. 1-5.

FIG. 18 is a perspective view of an exemplary portable sanitizing system 1300 for use with any combination of circuits 100, 110, 120, 130, and 140 shown in FIGS. 1-5 and FIG. 19 is a perspective view of an alternative portable sanitizing system 1400 for use with any combination of circuits 100, 110, 120, 130, and 140 shown in FIGS. 1-5. Systems 1300 and 1400 each include a computing device 1302 and a portable sanitizer 1304 and 1402 that is configured to removably couple to device 1302. In the exemplary embodiment, computing device 1302 is a handheld computing device including, but not limited to, smart watch, smartphone, tablet, laptop, or PC. Computing device 1302 includes a processor and camera (not shown). The system 1300 may further include sensors, such as sensor for the body, tissue, blood, other fluid, that are in communication with the computing device 1302.

Figure 19:
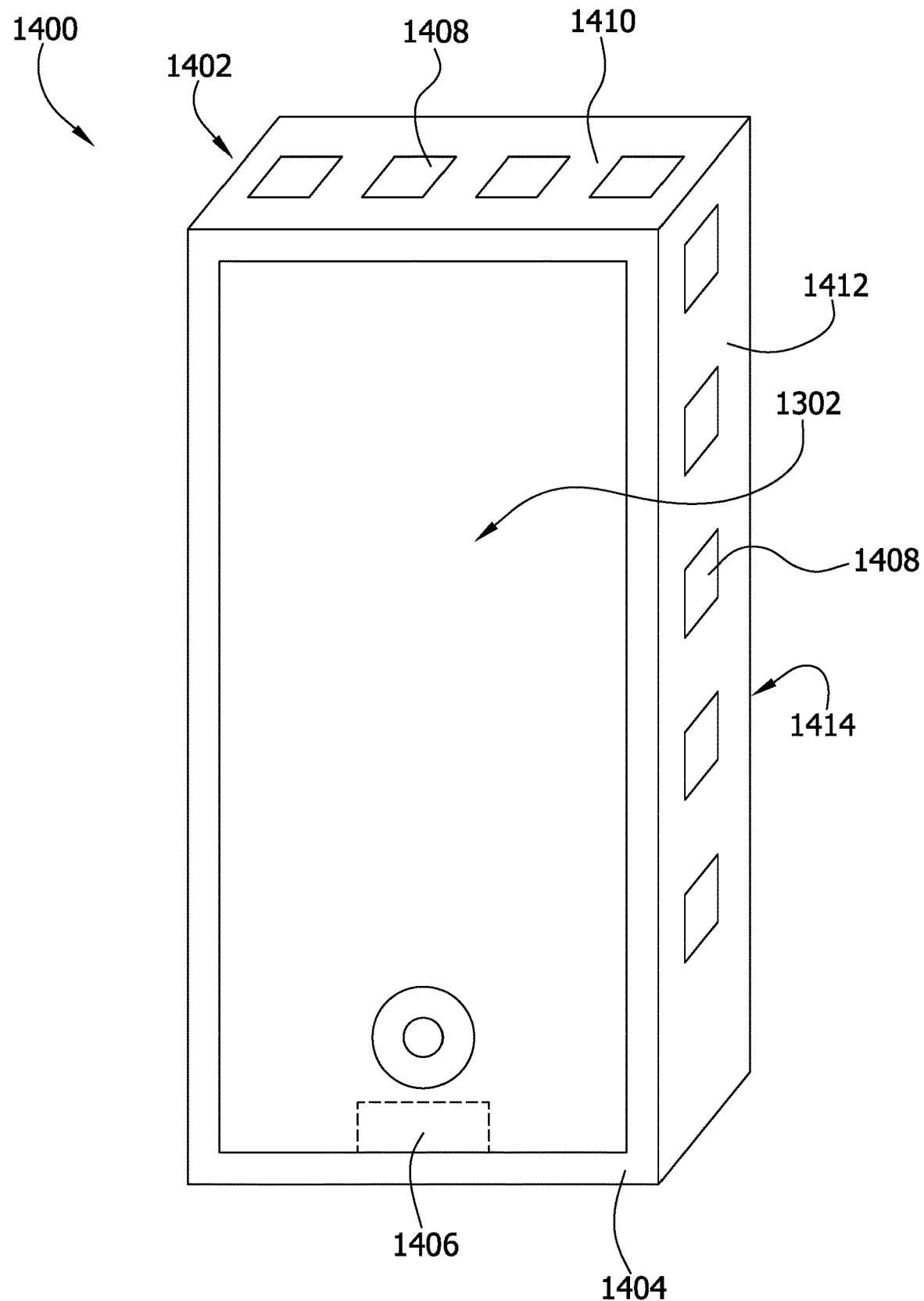
FIG. 19 is a perspective view of an alternative portable system for at least one of disinfecting, sanitizing, and sterilizing an object for use with any combination of the circuits shown in FIGS. 1-5.

Sanitizers 1304 and 1402 each include a housing 1306 and 1404 and an input jack 1308 and 1406 coupled to housing 1306 and 1404. Housing 1404 is configured to substantially encase the sides of device 1302. In the exemplary embodiment, input jack 1308 and 1406 is configured to be inserted into device 1302 to transfer information bi-directionally between device 1302 and sanitizer 1304 and 1402. In one embodiment, as shown in FIG. 18, the input jack can be a TRS (tip, ring, sleeve) or TRRS connector also known as an audio jack, phone jack, phone plug, and jack plug configured to insert into a line in/out 1310 or microphone socket of device 1302. Alternatively, as shown in FIG. 19, the input jack can be configured to insert into a power and/or communication port of device 1302.

Coupled in housing 1306 and 1404 is a power source (e.g. battery) that is coupled to light source 1312 and 1408 configured to emit UVC. Power source can be configured to be removably coupled to housing enabling a user to exchange or swap power sources (e.g. battery) from the housing. Additionally, the power source can be any power source configured to removably couple to the housing including, but not limited to, alkaline, lithium, and lithium-ion. Housing 1306 and 1404 can be configured to have a charging port that enables an external power source to provide current to the power source coupled in housing 1306 and 1404 to charge and/or power sanitizers 1304 and 1402. In one embodiment, light source 1312 and 1408 is ultraviolet LED, LED array, and/or laser. The depth of penetration of the light source may be controlled. Alternatively, light source 1312 and 1408 can be any light source that provides UVC waves. As shown in FIG. 19, light source 19 can be coupled anywhere to housing 1404 including a horizontal surface 1410, vertical surface 1412, and/or back panel surface 1414. Similarly, light source 1312 can be coupled to any surface of housing 1306.

In operation, sanitizers 1304 and 1402 receive power instructions from device 1302 and 1402. In the exemplary embodiment, devices 1302 and 1402 are configured to run an application that provides execution instructions to sanitizers 1304 and 1402. Likewise, the application is configured to receive information from sanitizers 1304 and 1402 and sensors associated with device 1302 and 1402 to provide execution instructions. For example, a user may select to run a sanitizing protocol for kitchen counters. The application would determine the amount, power, and duration of UVC needed to kill infectious agents associated with kitchen counters. The sanitizers 1304 and 1402 can be associated with a robot or other device for automatically moving the sanitizers during treatment session. It should be noted that infectious agent data could be pulled from a data source retained locally on device 1302 and 1404 or on a remote storage location that is communicatively coupled to the device.

Once the application has determined the amount, power, and duration of UVC required for a particular protocol, a session is initiated or held until a user interacts with device (e.g. starts the session). During the session, sensors (e.g. accelerometer, magnetometer, gyroscope, proximity sensor, and camera) in device 1302 and 1402 are utilized to provide feedback as to the effectiveness of the session. The application can alert a user as to whether a surface and/or object has been in contact with a surface long enough to be sterilized and/or if a rate of speed of the sanitizer 1304 and 1402 is too fast or too slow to achieve a desired result. The feedback can be in any form provided by device 1302 and 1402 including but not limited to, visual and auditory signals.

Figure 20:
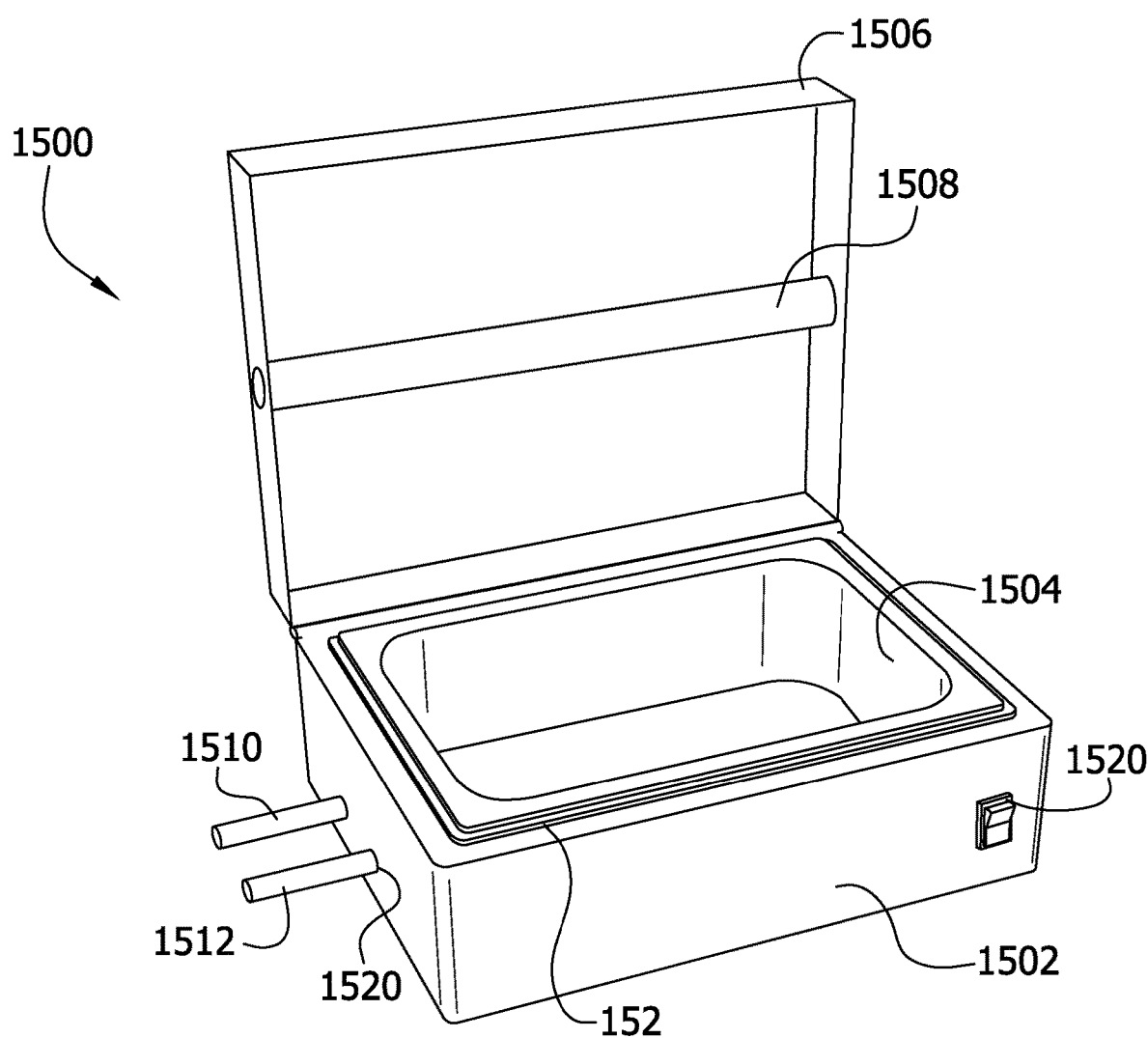
FIG. 20 is a perspective view of an exemplary a device for at least one of disinfecting, sanitizing, and sterilizing a surgical tool for use with any of the any combination of the circuits shown in FIGS. 1-5.

FIG. 20 is a perspective view of an exemplary surgical tool sterilizer 1500 for use with any of the any combination of circuits 100, 110, 120, 130, and 140 shown in FIGS. 1-5. Sterilizer 1500 includes a housing 1502 with an opening configured to receive a tub 1504 having a ultrasound transducer coupled to tub 1504. Housing 1502 includes a lid 1506 with a light source 1508 coupled thereto for emitting UVC. In the exemplary embodiment, light source 1508 is an ultraviolet LED, an LED array, or laser. Alternatively, light source 1508 can be any light source that provides UVC.

In one embodiment, an inlet 1510 and an outlet 1512 for fluid extends through housing 1502 and into tub 1504. Inlet 1510 and outlet 1512 may provide fresh fluid and fluid circulation before, during, and/or after a sterilization session. A pump may be connected to the inlet 1510 and/or a vacuum source may be connected to the outlet 1512. One or more valves may be connected to one or both of the inlet 1510 and the outlet 1512. A controller may control the filling of the tub 1504, and/or the circulation of the fluid, and/or the removal of the fluid from the tub. Alternatively, fluid may be manually provided to tub 1504 without the use of inlet 1510 and outlet 1512. In one embodiment, a switch 1514 is coupled to housing 1502 to initiate the use of the transducers and/or light source 1508. Alternatively, a remote device (e.g. smartphone, tablet, laptop, and PC) could provide instructions to sterilizer 1500.

In the exemplary embodiment, all components of sterilizer 1500 are sterilizable and seals and/or gaskets 1520 are used enable sterilizer 1500 to be autoclaved and placed in the sterile field during surgery. As such, electronics such as circuits 100, 110, 120, 130, and 140 could be kept outside the sterile field. In addition to cleaning and/or sterilizing surgical instruments, sterilizer 1500 could also be utilized to clean parts of a body, (e.g. treating or cleaning diabetic wounds) and sterilizing and/or cleaning food in an industrial or residential setting.

Any of FIGS. 6-20 can include reflective surfaces that enable a single light source to provide UVC to multiple surfaces and/or in different angles to objects being sterilized. For example, referring to FIG. 13, inner surface 872 of outer bowl 862 may have a reflective surface to provide UV throughout device 860 with the use of a single light source 876. Additionally, any of the light sources shown in FIGS. 6-20 can be configured to tilt, swivel, rotate, and/or move in any direction to provide a larger coverage area of the UV compared to a fixed light or beam. For example, referring to FIG. 9, light source 504 can be configured to move side to side (e.g. back and forth) as robot 500 travels over a floor. The treatment session time may vary for location, desired depth of penetration, and/or fluid opacity. Additionally, any of the light sources shown in FIGS. 6-20 can include a prism and/or balloon coupled to the light source to scatter light emanating from the light source.

In some embodiments, any of the embodiments in FIGS. 6-20 can include a presentation interface that is coupled to processor. The presentation interface is configured to present information, such as sterilization and/or timing information to a user. The presentation interface may include a display adapter (not shown) that may be coupled to a display device, such as a cathode ray tube (CRT), a liquid crystal display (LCD), an organic LED (OLED) display, and/or an "electronic ink" display. In some embodiments, the presentation interface includes one or more display devices.

In some embodiments, any of the embodiments in FIGS. 6-20 can include a user input interface that is coupled to a processor and receives input from user. The user input interface may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of the presentation interface and the user input interface. It should be noted that a UVC light source could provide UVC to the input interface to sterilize a surface used for input from a user.

It should be noted that any of the embodiments in FIGS. 6-20 can include a communication interface coupled to processor. The communication interface communicates with a remote device (e.g. smartphone, tablet, laptop, or PC) to provide sterilization information. To communicate with the remote device, communication interface may include, for example, a wired network adapter, a wireless network adapter, and/or a mobile telecommunications adapter (e.g. Bluetooth or cellular link).

All embodiments could be configured such that the optimal treatment time would be controlled via hardware or software so that the energy source would be disabled at the end of treatment. Treatment time can be selected and/or monitored via a remote device, the user input interface, or the presentation interface. In some embodiments, treatment times are selected based on the object being sterilized. Alternatively, treatment times can be selected based on the infectious agent that is intended to eliminate. In some embodiments, UVC is selected and transmitted in dosages provided in the following table to kill infectious agents. Alternatively, any dosage can be used that facilitates slowing growth and/or eliminating infectious agents. Moreover, the treatment may additionally include one or more of ultrasound transducer for producing vibratory energy, and laser for producing other light energy.

| Microorganism | Dosage mWs/cm$^2$ | UV Output 1 W/cm$^2$ (Seconds) | UV Output 5 W/cm$^2$ (Seconds) | UV Output 10 W/cm$^2$ (Seconds) |
|---|---|---|---|---|
| *Pencillium Roqueforti* | 28 | 28 | 6 | 3 |
| *Oospora Lactis* | 11 | 0 | 2 | 4 |
| Brewer's Yeast | 7 | 18 | 4 | 2 |
| *Saccharomyces Cerevislae* | 13 | 1 | 4 | 7 |
| *Strep Lactis* | 9 | 12 | 2 | 1 |
| *Staph. Aureus* | 7 | 1 | 3 | 6 |

-continued

| Microorganism | Dosage mWs/cm² | UV Output 1 W/cm² (Seconds) | UV Output 5 W/cm² (Seconds) | UV Output 10 W/cm² (Seconds) |
| --- | --- | --- | --- | --- |
| *Staph. Albus* | 6 | 11 | 2 | 1 |
| *Sarcina Lulea* | 26 | 2 | 12 | 25 |
| *Escerichia Coli* | 7 | 3 | 1 | 0 |
| *Bacillus Subtills* | 11 | 4 | 19 | 39 |
| Bacterlophage (*E. Coli*) | 7 | 2 | 0 | 0 |
| Influenza | 3 | 2 | 8 | 17 |
| Algae | 22 | 13 | 3 | 1 |
| *Proteus Vulgaris* | 8 | 1 | 3 | 6 |
| *N. fowleri* trophozoite | 13 | 22 | 4 | 2 |
| *N. fowleri* cyst | 63 | 3 | 15 | 29 |
| Cyptosporidium | 6 | 2 | 0 | 0 |
| Giardia | 5 | 2 | 12 | 24 |
| Adenovirus | 50 | 21 | 4 | 2 |
| Hepatitis A | 11 | 1 | 3 | 5 |
| *Acanthamoeba* | 71 | 133 | 27 | 13 |
| Influenza A | 4 | 0 | 0 | 0 |
| Vaccinia | 3 | 100 | 20 | 10 |
| Coxsakievirus | 4 | 0 | 0 | 0 |
| *Staphylococcus A* | 2 | 50 | 10 | 5 |
| Tuberculosis | 2 | 0 | 0 | 0 |
| *Legionella* | 2 | 50 | 10 | 5 |

Generally, UVC 260-340 nm can disrupt both DNA and RNA. This requires a specific direct line of site as well as a specific type. It has a depth of penetration. Treatment modalities would require this direct line of sight, specific time interval, depth of penetration, and specific exposure. This could be done through direct light, reflective light, specific movement or compression of the material so it becomes closer to the light source.

In addition, acoustic therapy/ultrasound can provide vibratory/debridement type treatment. This treatment in combination with UVC or in isolation may allow debridement material where similar modules can be removed or separated in existing ultrasonic cleaner or can be utilized in combination with chemical agents or pharmaceutical agents. Ultrasound may also have the potential to affect permeability of cell walls, membrane, i.e. bacterial cell walls, or blood brain barriers for example in dura which may enhance penetration of existing pharmaceutical or chemotherapy agents or chemical agents to enhance the ability to sterilize or clean tissue. Also the vibratory component may allow in combination with UVC less time or more direct light exposure.

UVC can be applied to traditional light, LED with battery operated, or laser to increase the depth of penetration. UVC can be battery powered or externally powered through electromagnetic waves to allow implantable device to be turned on or off. Ultraviolet light can have deleterious effects to other tissue as it can affect DNA and RNA. Pharmaceutical or other materials and/or chemicals, such as $H_2O_2$, may be added to the surface being treated.

The light optical or acoustic also has a depth of penetration, intensity of the light and duration. It could be integrated via computer and software programs to be able to turn on and off or be mobile. In addition, UVC and/or ultrasonic can be applied via robotic mechanism so they can be selectively moved whether in the body, in a room or specific space with a timer and location so one can provide timing/direct light of sight (reflective sight) or movement closer or farther as needed to enhance sterilization for topical effect. UVC could be applied via robotic control such as robotic floor cleaner or surface cleaner or via remote control drone type of device. It could also have motion sensors that could allow when movement is detected to be turned on or off so it is not damaging any living tissue in animals, people, etc.

This single or composite treatment may have use of pharmaceuticals (i.e. antibiotics or bacteriocidal) or can enhance the efficacy of the effect of pharmaceutical by applying UVC, ultrasound treatment, composite treatment, acoustic treatment, and/or optical treatment to enhance the efficacy of target agent for pharmaceutical. For example, ultrasound may open the cell wall membranes or bacterial wall membranes previously persistent antibiotics now can become toxic to the bacteria via the application of UVC or acoustic/ultrasound phenomenon. Vibratory or optical treatments may open the cell wall membranes to allow pharmaceutical/chemical agents to penetrate where previously the bacteria or cells were resistance to this and allow better depth of penetration. Resistant pharmaceutical agents may now become toxic to the bacteria, viruses, parasites, etc. Individuals could wear shields to eyes such as specific sunglasses to tune out UV or it could be motion censored or detect heat/movement to turn on or off either via remote control or via computer control. This could be linked to a control system that could also allow local pharmaceutical/chemotherapeutic agents whether inside the body or on a specific surface. We could also time so that chemical agents and/or UVC could be administered simultaneously i.e. spraying 60% alcohol and/or $H_2O_2$ as well as UVC at the same time so it would coat a body surface to sterilize it. This could be used for example for gloves which are placed on individual's hands. The gloves could have an optical shield in them so the UVC would not penetrate through the gloves. The individual would wear gloves and for example work on a patient rather than changing gloves and going to the next patient. They would go under a shield where UVC would be applied and then spray 60% alcohol or greater preparation that would further sterilize the gloves. These would also be dried and then one could go on to the next patient. This would prevent damage to the skin as the gloves would be on and the gloves would have an opaque surface for UVC so that UVC would not penetrate through the skin with addition of alcohol or chemical agent to further sterilize from above and below so circumferential treatment of gloves so one would not have to change gloves constantly. The gloves intrinsically would have an agent that would prevent penetration of UVC into the skin or tissue. As UVC is applied, it would either be shielded or be opaque so one would simply scan their hands for a known period of time underneath this for light and/or chemical agent to be sprayed on. Either the movement alone would allow drying or there could be a small burst of air with fan, etc. that would dry this. The combination of two agents would then allow the gloves to be sterilized so that one would not have to change the gloves and can keep the gloves on when going from patient-to-patient or treatment-to-treatment with preparation, etc.

If one has solid debris, one could place it in a vibratory ultrasonic bath. The ultrasonic bath could have chemical agents in it, pharmaceutical agents, etc. or could simply vibrate the material. One could then pass under UVC so composite treatments would not only debride and move material but then also sterilize UVC. It also affects not just bacteria but would affect viruses, parasites, or any material that is RNA/DNA. There would need to be a specific type typically in range of second and then with or without chemical or pharmaceutical spray and then we would be able to utilize.

This could also be applied for example in the eye. Currently, Toxoplasma gondii is a toxic infection in the eye and can permanently damage retinal cells. Antibiotics have trouble going to the blood brain barrier and there is no treatment as these agents can hide within the parasites/toxoplasmosis. With UVC/laser, one could go through the eye and treat the parasites for a period of a second or two.

It would focus on specific lesions that may have active parasites and selectively kill these. Otherwise, it is extremely difficult to assess. Otherwise, these are permanent parasites. This could also be used for target laser and other type of parasites. It would not allow visualization but endoscopically for example light source could be applied to the liver, cranial tissue, brain tissue, liver tissue, etc. where parasites/viruses live permanently. This could be effective for herpes type viruses and neurologic tissue and specifically target the parasitic DNA. Specific timers and energy frequencies could be utilized to avoid damaging body tissue while specifically focusing on RNA or DNA of the parasitic tissue, viral tissue, or bacteria. Again, this could be used with known pharmaceutical treatment or could be used in isolation. The vibratory or acoustic components could also be applied to provide further access especially if there is fluid or gelatin media could be applied. This could be staged or simultaneous.

If one is adopting the pill or agent which could be implanted or swallowed to effect local tissue, the acoustic/optical energy UVC could be turned on or off as needed. There could also be remote control so the pill could be sped up or slowed down for example to adjust the system rather than allowing normal parasitosis to push the pill through the digestive system. This could be slowed by external wavelengths or radiofrequency so they can move either with parasitosis faster or slower so it could target a specific location. There could also be timer for turning the acoustic/optical energy UVC on and/or off.

This could be implanted in the peritoneum. For example, it could be guided in the peritoneum either robotically or magnetically to a specific location for a specific period of time. This would allow optical/acoustic energy. This could also time release a pharmaceutical agent as well so this could be timed and moved to another location. This could be done under endoscopic guidance during a surgical procedure or this could be implanted surgically and then applied at specific intervals. Later, this device could be tracked and then removed either by MRI, x-ray, ultrasound, or other diagnostic. This could be implanted laparoscopically, endoscopically, arthroscopically into the joint. It could be used, for example, arthroscopically into a joint if one has calcium (chondrocalcinosis crystals) that coat the joint one could use this to move through the joint and selectively remove the calcium crystals from the articular cartilage. This could be selectively removed with vibratory frequencies over a period of time so it would not damage the articular cartilage cells but acoustically, optically, chemically, or with pharmaceutical agents could selectively release the calcium crystals so they can move to the articular cartilage. One could have articular cartilage previously damaged via coating of chondrocalcinosis crystals. This would selectively vibrate and remove the crystals. There are different modules or elasticity of calcium which would selectively be removed and then potentially be flushed out again through a surgical procedure or could be left inside the joint. As one moves, it could selectively go through different parts of the joint and selectively move either from cartilage, synovial tissue, etc. This could target other known coating agents i.e. biofilm. Biofilm has different module so elasticity and biofilm can separate from tissue such as a joint replacement. Acoustic energy with or without UVC could be applied. Again, this could be implanted, removed, placed during endoscopic or arthroscopic procedure. It could then be selectively turned on and off to selectively remove the biofilm, chondrocalcinosis, or other material coating from metallic implant, polymeric implant, or biologic tissue since they are different modules and different material. They would selectively separate. This could be flushed out with chemotherapy or pharmaceutical agents. This could also be used to separate tumor which is a rapidly growing cell that is typically stiffer, harder, and firmer than local tissue. One could use the UVC, ultrasound, and/or chemotherapeutic agents to selectively kill the stiffer tissue i.e. rapidly growing neoplasm/cancerous tissue. Since it is rapidly growing, DNA is more affected by UVC and RNA affected by UVC ultrasound, chemotherapeutic agents where this could be targeted and turned on/off selectively as diagnostic portion of ultrasound will measure the density of the tissue. The acoustic portion of ultrasound will separate the two and then either ultrasound UVC and/or chemotherapeutic agent applied locally to kill neoplastic tissue. This could then selectively be turned on/off depending on the diagnostic portion of the ultrasound which in frequency determines there is a slime i.e. biofilm, chondrocalcinosis, crystallin type tissue, or denser tissue i.e. rapidly growing tumor tissue that has different acoustic density or diagnostic density via MM or other diagnostic test. This could be selectively turned on and off with implantable or surgically operated device. This could be robotically controlled externally. Other treatments can also be applied, including laser (optical), electrical (RF), mechanical (pressure, torque), ESW, chemical (ETOH, $H_2O_2$), and pharmaceutical (pH/acid based).

Examples of this are implied in other patents i.e. Bonutti Robotics, Bonutti MIS patents which we reference by incorporation.

This also could be applied locally to tissue or locally to surfaces via wireless or mobile phone—Smartphone technology. UVC could be built on or application for your mobile phone where a selective wavelength could be used via cellphone, mobile device, Ipad, etc. to treat a specific surface. There would be a timer, location, depth. It would measure the distance from a specific surface. It would turn this on or off. It would be shielded so it would not develop direct eye contact. It could sterilize, cleanse, treat surface via UVC and mobile phone. Mobile application could also be used as a treatment device to turn on/off implantable device within the human body for sterilization treatment, chemotherapy, treatment of biofilm, etc. It could potentially be used to power the device. Chemotherapy agents or pharmaceutical agents could be applied by spraying, direct pressure, or solution to specific tissue as well.

The embodiments described herein enable provide a cost effective manner for sterilizing objects. As compared to at least some known sterilization systems, the systems and methods described herein enable a user to sanitize, disinfect, and/or clean surfaces and/or objects without the use of chemical agents. In applications where the water will be consumed, the UV treatment would also be remove chlorine aftertaste in the water providing safe drinking water that is free of infectious agents.

The embodiments described herein may utilize executable instructions embodied in a non-transitory computer readable medium, including, without limitation, a storage device or a memory area of a computing device. Such instructions, when executed by one or more processors, cause the processor(s) to perform at least a portion of the methods described herein. As used herein, a "storage device" is a tangible article, such as a hard drive, a solid state memory device, and/or an optical disk that is operable to store data.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims

What is claimed is:

1. A disinfecting system comprising:
   a sanitizer including a housing, and an ultraviolet light (UV) source secured to the housing and configured to emit UV light for disinfection of a target; and
   a smartphone including a processor,
   wherein the sanitizer is removably and physically coupled to the smartphone, and wherein the processor is in communication with the sanitizer and configured to activate the UV light source for a selected amount of time suitable for disinfection of the target.

2. The disinfecting system set forth in claim 1, wherein the UV light source is configured to emit UV light having a wavelength from about 100 nm to about 400 nm.

3. The disinfecting system set forth in claim 2, wherein the UV light source is configure to emit UV light having a wavelength from about 240 nm to about 260 nm.

4. The disinfecting system set forth in claim 2, in combination with an ultrasound transducer configured to emit ultrasonic energy for disinfecting the target.

5. The disinfecting system set forth in claim 2, wherein the UV light source comprises an ultraviolet LED.

6. The disinfecting system set forth in claim 2, wherein the UV light source comprises a laser.

7. The disinfecting system set forth in claim 1, wherein the sanitizer further includes a jack inserted into a port of the smartphone.

8. The disinfecting system set forth in claim 7, wherein the jack is inserted into a power port of the smartphone.

9. A sanitizer for disinfecting, the sanitizer comprising:
   a sanitizer including a housing, and an ultraviolet light (UV) source secured to the housing and configured to emit UV light for disinfection of a target,
   wherein the sanitizer is configured to be removably and physically coupled to a smartphone,
   wherein the sanitizer is configured to be in communication with the smartphone and receive instructions from the smartphone to activate the UV light source for a selected amount of time suitable for disinfection of the target.

10. The sanitizer for disinfecting set forth in claim 9, wherein the sanitizer further includes a jack configured to be inserted into a port of the smartphone.

11. The sanitizer for disinfecting set forth in claim 10, wherein the jack is configured to be inserted into a power port of the smartphone.

12. The disinfecting system set forth in claim 9, wherein the UV light source is configured to emit UV light having a wavelength from about 100 nm to about 400 nm.

13. The sanitizer for disinfecting set forth in claim 12, wherein the UV light source is configure to emit UV light having a wavelength from about 240 nm to about 260 nm.

14. The sanitizer for disinfecting set forth in claim 12, in combination with an ultrasound transducer configured to emit ultrasonic energy for disinfecting the target.

15. The sanitizer for disinfecting set forth in claim 12, wherein the UV light source comprises an ultraviolet LED.

16. The sanitizer for disinfecting set forth in claim 12, wherein the UV light source comprises a laser.

* * * * *